United States Patent
Altarac et al.

(10) Patent No.: US 10,512,547 B2
(45) Date of Patent: Dec. 24, 2019

(54) INTERBODY SPACER

(71) Applicant: NEUROSTRUCTURES, INC., Irvine, CA (US)

(72) Inventors: Moti Altarac, Irvine, CA (US); Joey Reglos, Lake Forest, CA (US); Babak Barcohana, Los Angeles, CA (US)

(73) Assignee: NeuroStructures, Inc., Irvine, CA (US)

(*) Notice: Subject to any disclaimer, the term of this patent is extended or adjusted under 35 U.S.C. 154(b) by 132 days.

(21) Appl. No.: 15/587,240

(22) Filed: May 4, 2017

(65) Prior Publication Data
US 2018/0318100 A1     Nov. 8, 2018

(51) Int. Cl.
*A61F 2/44*     (2006.01)
*A61F 2/30*     (2006.01)
*F16B 21/02*     (2006.01)

(52) U.S. Cl.
CPC .. *A61F 2/4455* (2013.01); *A61F 2002/30482* (2013.01); *A61F 2002/30495* (2013.01); *A61F 2002/30497* (2013.01); *A61F 2002/30528* (2013.01); *F16B 21/02* (2013.01)

(58) Field of Classification Search
CPC ...... A61F 2/442; A61F 2/4455; A61F 2/4465; A61F 2002/30772; A61F 2002/4475; A61F 2002/30787; A61F 2002/30476; A61F 2002/30528; A61F 2002/3085; A61B 17/7059; A61B 17/8042; A61B 17/8033; A61B 17/7074; F16B 21/02; F16B 41/002
USPC ................ 606/289, 292–293, 295–296, 288; 623/17.11–17.16; 411/999, 349
See application file for complete search history.

(56) References Cited

U.S. PATENT DOCUMENTS

| | | | |
|---|---|---|---|
| 3,554,075 A | * | 1/1971 | Johnson ................. F16B 21/04 411/349 |
| 3,741,205 A | | 6/1973 | Markoff et al. |
| 5,085,660 A | | 2/1992 | Lin |
| 5,364,399 A | | 11/1994 | Lowery et al. |
| 5,423,826 A | | 6/1995 | Coates et al. |
| 5,549,612 A | | 8/1996 | Yapp et al. |
| 5,616,142 A | | 4/1997 | Yuan et al. |

(Continued)

FOREIGN PATENT DOCUMENTS

| EP | 1520545 B1 | 11/2006 |
|---|---|---|
| EP | 1429675 B1 | 10/2007 |

(Continued)

*Primary Examiner* — David W Bates
*Assistant Examiner* — Marcela I Shirsat
(74) *Attorney, Agent, or Firm* — Rimas T. Lukas

(57) ABSTRACT

An interbody spacer for the spine is provided. The interbody spacer includes a cage and at least one bone screw configured to anchor the cage between two vertebrae of the spine. The cage includes a lock rotationally movable with respect to the cage between a locked configuration and an unlocked configuration. When in an unlocked configuration, bone screws may be inserted and removed from the cage. When in a locked configuration, the insertion and removal pathway of the bone screw is blocked by the lock, thereby, providing backout protection for the bone screws. The lock is coupled to the cage by a retaining ring. The lock assembly also includes a timing lock to provide for incremental rotation of the lock. The lock includes a space-saving shape providing for maximum bone screw angulation on a laterally smaller anterior platform.

8 Claims, 14 Drawing Sheets

(56) References Cited

U.S. PATENT DOCUMENTS

| | | | |
|---|---|---|---|
| 5,616,144 A | 4/1997 | Yapp et al. | |
| 5,676,483 A * | 10/1997 | Koubek | A47C 1/03 |
| | | | 297/411.36 |
| 6,045,552 A | 4/2000 | Zucherman et al. | |
| 6,070,294 A * | 6/2000 | Perkins | A47K 3/36 |
| | | | 16/250 |
| 6,139,550 A | 10/2000 | Michelson | |
| 6,398,783 B1 | 6/2002 | Michelson | |
| 6,527,776 B1 | 3/2003 | Michelson | |
| 6,599,290 B2 | 7/2003 | Bailey et al. | |
| 6,602,255 B1 | 8/2003 | Campbell et al. | |
| 6,626,907 B2 | 9/2003 | Campbell et al. | |
| 6,652,525 B1 | 11/2003 | Assaker et al. | |
| 6,695,846 B2 | 2/2004 | Richelsoph et al. | |
| 6,926,718 B1 | 8/2005 | Michelson | |
| 6,936,051 B2 | 8/2005 | Michelson | |
| 6,964,664 B2 | 11/2005 | Fried et al. | |
| 7,175,623 B2 | 2/2007 | Thramann et al. | |
| 7,186,254 B2 | 3/2007 | Dinh et al. | |
| 7,220,263 B2 | 5/2007 | Cordaro | |
| 7,273,481 B2 | 9/2007 | Lombardo et al. | |
| 7,276,070 B2 | 10/2007 | Muckter | |
| 7,278,997 B1 | 10/2007 | Mueller et al. | |
| 7,288,094 B2 | 10/2007 | Lindemann et al. | |
| 7,288,095 B2 | 10/2007 | Baynham et al. | |
| 7,291,152 B2 | 11/2007 | Abdou | |
| 7,306,605 B2 | 12/2007 | Ross | |
| 7,318,825 B2 | 1/2008 | Butler et al. | |
| 7,524,325 B2 | 4/2009 | Khalili | |
| 7,601,170 B2 | 10/2009 | Winslow et al. | |
| 7,651,517 B2 | 1/2010 | Konieczynski et al. | |
| 7,662,154 B2 | 2/2010 | Ribeiro | |
| 7,686,806 B2 | 3/2010 | Rhyne | |
| 7,704,255 B2 | 4/2010 | Michelson | |
| 7,740,630 B2 | 6/2010 | Michelson | |
| 7,803,157 B2 | 9/2010 | Michelson | |
| 7,811,285 B2 | 10/2010 | Michelson | |
| 7,815,666 B2 | 10/2010 | Baynham et al. | |
| 7,824,432 B2 | 11/2010 | Michelson | |
| 7,887,547 B2 | 2/2011 | Campbell et al. | |
| 8,048,075 B2 | 11/2011 | Michelson | |
| 8,206,293 B2 | 6/2012 | Reglos et al. | |
| 8,439,924 B1 | 5/2013 | McBride et al. | |
| 8,460,308 B2 | 6/2013 | Marino et al. | |
| 8,480,747 B2 * | 7/2013 | Melkent | A61F 2/442 |
| | | | 623/17.11 |
| 8,652,182 B1 | 2/2014 | Walker et al. | |
| 8,668,723 B2 | 4/2014 | Zhang et al. | |
| 9,743,958 B2 | 8/2017 | Ishii et al. | |
| 10,016,224 B2 | 7/2018 | Altarac et al. | |
| 2002/0120270 A1 | 8/2002 | Trieu et al. | |
| 2003/0060828 A1 | 3/2003 | Michelson | |
| 2003/0093082 A1 | 5/2003 | Campbell et al. | |
| 2003/0105462 A1 | 6/2003 | Haider | |
| 2003/0105466 A1 | 6/2003 | Ralph et al. | |
| 2003/0105467 A1 | 6/2003 | Ralph et al. | |
| 2003/0125739 A1 | 7/2003 | Bagga et al. | |
| 2003/0135216 A1 | 7/2003 | Sevrain | |
| 2003/0153920 A1 | 8/2003 | Ralph et al. | |
| 2003/0171753 A1 | 9/2003 | Collins et al. | |
| 2003/0181912 A1 | 9/2003 | Michelson | |
| 2003/0187440 A1 | 10/2003 | Richelsoph et al. | |
| 2003/0187442 A1 | 10/2003 | Richelsoph et al. | |
| 2003/0187509 A1 | 10/2003 | Lemole, Jr. | |
| 2003/0191471 A1 | 10/2003 | Michelson | |
| 2003/0191472 A1 | 10/2003 | Michelson | |
| 2003/0208204 A1 | 11/2003 | Bailey et al. | |
| 2003/0229348 A1 | 12/2003 | Sevrain | |
| 2003/0236528 A1 | 12/2003 | Thramann | |
| 2004/0006343 A1 | 1/2004 | Sevrain | |
| 2004/0015169 A1 | 1/2004 | Gause | |
| 2004/0019353 A1 | 1/2004 | Freid et al. | |
| 2004/0024081 A1 | 2/2004 | Trieu et al. | |
| 2004/0030336 A1 | 2/2004 | Khanna | |
| 2004/0034352 A1 | 2/2004 | Needham et al. | |
| 2004/0039387 A1 | 2/2004 | Gause et al. | |
| 2004/0049279 A1 | 3/2004 | Sevrain | |
| 2004/0068319 A1 | 4/2004 | Cordaro | |
| 2004/0087945 A1 | 5/2004 | Ralph et al. | |
| 2004/0087951 A1 | 5/2004 | Khalili | |
| 2004/0092929 A1 | 5/2004 | Zindrick | |
| 2004/0092947 A1 | 5/2004 | Foley | |
| 2004/0097925 A1 | 5/2004 | Boehm, Jr. et al. | |
| 2004/0097934 A1 | 5/2004 | Farris et al. | |
| 2004/0097935 A1 | 5/2004 | Richelsoph et al. | |
| 2004/0097938 A1 | 5/2004 | Alleyne | |
| 2004/0097950 A1 | 5/2004 | Foley et al. | |
| 2004/0106924 A1 | 6/2004 | Ralph et al. | |
| 2004/0122426 A1 | 6/2004 | Michelson | |
| 2004/0127897 A1 | 7/2004 | Freid et al. | |
| 2004/0127899 A1 | 7/2004 | Konieczynski et al. | |
| 2004/0127900 A1 | 7/2004 | Konieczynski et al. | |
| 2004/0133205 A1 | 7/2004 | Thramann et al. | |
| 2004/0153088 A1 | 8/2004 | Ralph et al. | |
| 2004/0158246 A1 | 8/2004 | Assaker et al. | |
| 2004/0177847 A1 | 9/2004 | Foley et al. | |
| 2004/0181226 A1 | 9/2004 | Michelson | |
| 2004/0181229 A1 | 9/2004 | Michelson | |
| 2004/0186476 A1 | 9/2004 | Michelson | |
| 2004/0204710 A1 | 10/2004 | Patel et al. | |
| 2004/0204712 A1 | 10/2004 | Kolb et al. | |
| 2004/0204713 A1 | 10/2004 | Abdou | |
| 2004/0210314 A1 | 10/2004 | Michelson | |
| 2004/0215192 A1 | 10/2004 | Justis et al. | |
| 2004/0215195 A1 | 10/2004 | Shipp et al. | |
| 2004/0220571 A1 | 11/2004 | Assaker et al. | |
| 2004/0220572 A1 | 11/2004 | Michelson | |
| 2004/0225290 A1 | 11/2004 | Ferree | |
| 2004/0236333 A1 | 11/2004 | Lin | |
| 2004/0236334 A1 | 11/2004 | Michelson | |
| 2004/0236335 A1 | 11/2004 | Michelson | |
| 2004/0243128 A1 | 12/2004 | Howland | |
| 2004/0260306 A1 | 12/2004 | Fallin et al. | |
| 2005/0015092 A1 | 1/2005 | Rathbun et al. | |
| 2005/0015093 A1 | 1/2005 | Suh et al. | |
| 2005/0027296 A1 | 2/2005 | Thramann et al. | |
| 2005/0027297 A1 | 2/2005 | Michelson | |
| 2005/0027298 A1 | 2/2005 | Michelson | |
| 2005/0033298 A1 | 2/2005 | Hawkes et al. | |
| 2005/0038436 A1 | 2/2005 | Michelson | |
| 2005/0043732 A1 | 2/2005 | Dalton | |
| 2005/0059970 A1 | 3/2005 | Kolb | |
| 2005/0059971 A1 | 3/2005 | Michelson | |
| 2005/0075633 A1 | 4/2005 | Ross | |
| 2005/0085816 A1 | 4/2005 | Michelson | |
| 2005/0137597 A1 | 6/2005 | Butler et al. | |
| 2005/0149021 A1 | 7/2005 | Tozzi | |
| 2005/0149026 A1 | 7/2005 | Butler et al. | |
| 2005/0149027 A1 | 7/2005 | Campbell et al. | |
| 2005/0171551 A1 | 8/2005 | Sukovich et al. | |
| 2005/0177160 A1 | 8/2005 | Baynham et al. | |
| 2005/0177161 A1 | 8/2005 | Baynham et al. | |
| 2005/0177163 A1 | 8/2005 | Abdou | |
| 2005/0187552 A1 | 8/2005 | Michelson | |
| 2005/0187553 A1 | 8/2005 | Grabowski et al. | |
| 2005/0187554 A1 | 8/2005 | Michelson | |
| 2005/0192576 A1 | 9/2005 | Michelson | |
| 2005/0208095 A1 | 9/2005 | Hunter et al. | |
| 2005/0209593 A1 | 9/2005 | Kolb | |
| 2005/0216005 A1 | 9/2005 | Howland | |
| 2005/0216009 A1 | 9/2005 | Michelson | |
| 2005/0216010 A1 | 9/2005 | Michelson | |
| 2005/0228386 A1 | 10/2005 | Ziolo et al. | |
| 2005/0234455 A1 | 10/2005 | Binder et al. | |
| 2005/0261690 A1 | 11/2005 | Binder et al. | |
| 2005/0273105 A1 | 12/2005 | Konieczynski et al. | |
| 2005/0277930 A1 | 12/2005 | Parsons | |
| 2005/0277938 A1 | 12/2005 | Parsons | |
| 2006/0009845 A1 | 1/2006 | Chin | |
| 2006/0030852 A1 | 2/2006 | Sevrain | |
| 2006/0079961 A1 | 4/2006 | Michelson | |
| 2006/0082015 A1 | 4/2006 | Happonen et al. | |
| 2006/0085001 A1 | 4/2006 | Michelson | |
| 2006/0149251 A1 | 7/2006 | Ziolo et al. | |

(56) References Cited

U.S. PATENT DOCUMENTS

| | | |
|---|---|---|
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200146 A1 | 9/2006 | Doubler et al. |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |
| 2006/0241616 A1 | 10/2006 | Konieczynski et al. |
| 2006/0276792 A1 | 12/2006 | Ensign et al. |
| 2006/0287653 A1 | 12/2006 | Rhyne |
| 2007/0083203 A1 | 4/2007 | Ribeiro |
| 2007/0123884 A1 | 5/2007 | Abdou |
| 2007/0167954 A1 | 7/2007 | Sicvol et al. |
| 2007/0185489 A1 | 8/2007 | Abdou |
| 2007/0203492 A1 | 8/2007 | Needham et al. |
| 2007/0213728 A1 | 9/2007 | Lindemann et al. |
| 2007/0213729 A1 | 9/2007 | Lindemann et al. |
| 2007/0213820 A1 | 9/2007 | Magerl et al. |
| 2007/0213828 A1 | 9/2007 | Trieu et al. |
| 2007/0225707 A1 | 9/2007 | Wisnewski et al. |
| 2007/0225717 A1 | 9/2007 | Hawkes |
| 2007/0225718 A1 | 9/2007 | Ensign |
| 2007/0233070 A1 | 10/2007 | Young |
| 2007/0233072 A1 | 10/2007 | Dickinson et al. |
| 2007/0233107 A1 | 10/2007 | Zielinski |
| 2007/0233108 A1 | 10/2007 | Stalcup et al. |
| 2007/0233110 A1 | 10/2007 | Muhanna et al. |
| 2007/0233117 A1 | 10/2007 | Butler et al. |
| 2007/0233118 A1 | 10/2007 | McLain |
| 2007/0233119 A1 | 10/2007 | Markworth |
| 2007/0233120 A1 | 10/2007 | Thramann et al. |
| 2007/0239158 A1 | 10/2007 | Trieu et al. |
| 2007/0270851 A1 | 11/2007 | Erickson et al. |
| 2007/0270965 A1 | 11/2007 | Ferguson |
| 2007/0276371 A1 | 11/2007 | Baynham et al. |
| 2007/0276405 A1 | 11/2007 | Huebner et al. |
| 2008/0021470 A1 | 1/2008 | Ross |
| 2008/0051794 A1 | 2/2008 | Dec et al. |
| 2008/0208260 A1 | 8/2008 | Truckai et al. |
| 2008/0208262 A1 | 8/2008 | Butler et al. |
| 2008/0208263 A1 | 8/2008 | Butler et al. |
| 2008/0208341 A1 | 8/2008 | McCormack et al. |
| 2008/0215097 A1 | 9/2008 | Ensign et al. |
| 2008/0228226 A1 | 9/2008 | Shamie |
| 2008/0228230 A1 | 9/2008 | Ferree |
| 2008/0234680 A1 | 9/2008 | Zaiser et al. |
| 2008/0234681 A1 | 9/2008 | Baynham |
| 2008/0234689 A1 | 9/2008 | Melkent et al. |
| 2008/0234748 A1 | 9/2008 | Wallenstein et al. |
| 2008/0234749 A1 | 9/2008 | Forstein |
| 2008/0234750 A1 | 9/2008 | Woods et al. |
| 2008/0234751 A1 | 9/2008 | McClintock |
| 2008/0234752 A1 | 9/2008 | Dahners |
| 2008/0234753 A1 | 9/2008 | Trieu |
| 2008/0234755 A1 | 9/2008 | Henderson et al. |
| 2008/0269806 A1 | 10/2008 | Zhang et al. |
| 2008/0287999 A1 | 11/2008 | Markworth |
| 2008/0288001 A1 | 11/2008 | Cawley et al. |
| 2009/0131988 A1 | 5/2009 | Bush, Jr. et al. |
| 2009/0149888 A1 | 6/2009 | Abdelgany |
| 2009/0171397 A1 | 7/2009 | Rothman et al. |
| 2009/0177237 A1 | 7/2009 | Zucherman et al. |
| 2009/0177239 A1 | 7/2009 | Castro |
| 2009/0182341 A1 | 7/2009 | Link et al. |
| 2009/0182383 A1 | 7/2009 | Prybyla et al. |
| 2009/0187218 A1 | 7/2009 | Schaffhausen |
| 2009/0192549 A1 | 7/2009 | Sanders et al. |
| 2009/0210008 A1 | 8/2009 | Butler et al. |
| 2009/0222049 A1 | 9/2009 | Frigg et al. |
| 2009/0259226 A1 | 10/2009 | Michelson |
| 2009/0270926 A1 | 10/2009 | Hawkes |
| 2010/0016901 A1 | 1/2010 | Robinson |
| 2010/0042159 A1 | 2/2010 | Butler |
| 2010/0049256 A1 | 2/2010 | Jeon et al. |
| 2010/0057206 A1* | 3/2010 | Duffield .............. A61F 2/442 623/17.16 |
| 2010/0069968 A1 | 3/2010 | Assaker et al. |
| 2010/0234897 A1 | 9/2010 | Fisher et al. |
| 2010/0312279 A1 | 12/2010 | Gephart et al. |
| 2011/0054528 A1 | 3/2011 | Michelson |
| 2011/0106159 A1 | 5/2011 | Nazeck |
| 2011/0118784 A1 | 5/2011 | Baynham et al. |
| 2011/0190770 A1 | 8/2011 | Suh |
| 2011/0230885 A1 | 9/2011 | Weiner et al. |
| 2011/0313477 A1 | 12/2011 | McLean et al. |
| 2012/0109208 A1 | 5/2012 | Justis et al. |
| 2012/0245690 A1 | 9/2012 | Cowan, Jr. et al. |
| 2013/0023936 A1 | 1/2013 | Altarac et al. |
| 2013/0046345 A1 | 2/2013 | Jones et al. |
| 2013/0060294 A1 | 3/2013 | Donahue |
| 2013/0245705 A1 | 9/2013 | McBride et al. |
| 2013/0261679 A1 | 10/2013 | McBride et al. |
| 2013/0331892 A1 | 12/2013 | Peterson et al. |
| 2014/0142632 A1 | 5/2014 | Keyer et al. |
| 2014/0148860 A1 | 5/2014 | Rinner |
| 2014/0277145 A1 | 9/2014 | Reiblat et al. |
| 2014/0277206 A1 | 9/2014 | Reitblat et al. |
| 2015/0039035 A1 | 2/2015 | Kruger |
| 2016/0022317 A1 | 1/2016 | Kraus |
| 2018/0318099 A1* | 11/2018 | Altarac .............. A61F 2/442 |

FOREIGN PATENT DOCUMENTS

| | | |
|---|---|---|
| EP | 1841376 A2 | 10/2007 |
| EP | 1847229 A2 | 10/2007 |
| WO | WO2006076422 A2 | 7/2006 |
| WO | WO2007037774 A1 | 4/2007 |
| WO | WO2007101266 A1 | 9/2007 |
| WO | WO2007103081 A2 | 9/2007 |
| WO | WO2007121080 A2 | 10/2007 |
| WO | WO2006138291 B1 | 11/2007 |
| WO | WO2007134199 A2 | 11/2007 |
| WO | WO2009089395 A2 | 7/2009 |
| WO | WO2009091770 A1 | 7/2009 |
| WO | WO2009091775 A2 | 7/2009 |

* cited by examiner

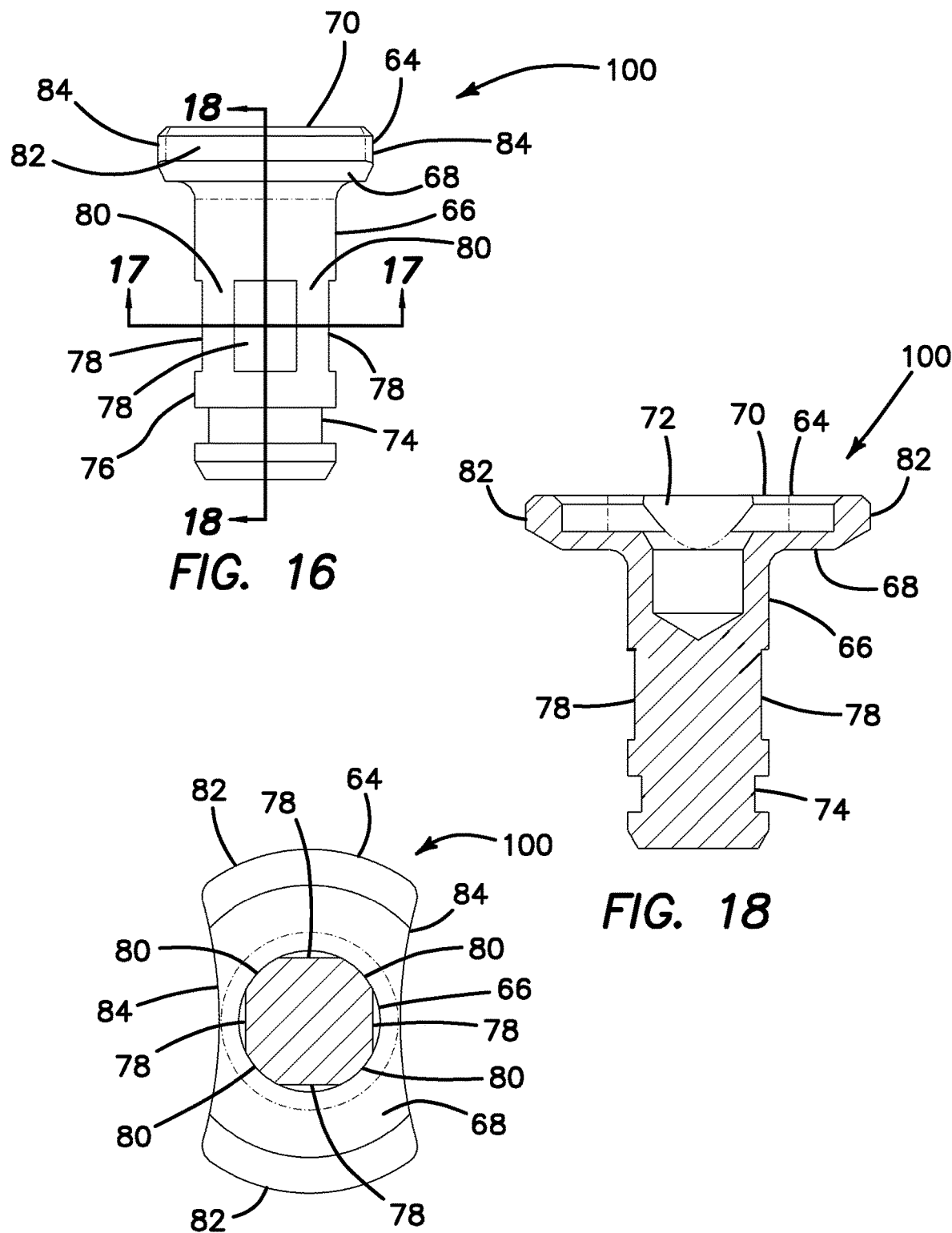

INTERBODY SPACER

FIELD OF THE INVENTION

This application relates generally to spinal implants, and in particular, intervertebral spacers and fusion cages.

BACKGROUND OF THE INVENTION

Back pain can be caused by a variety of factors including but not limited to the rupture or degeneration of one or more intervertebral discs due to degenerative disc disease, spondylolisthesis, deformative disorders, trauma, tumors and the like. In such cases, pain typically results from compression or irritation of spinal nerve roots arising from reduced spacing between adjacent vertebrae, a damaged disc and or misalignment of the spine resulting from the injury or degeneration.

Common forms of treating such pain include various types of surgical procedures in which a damaged disc may be partially or totally excised. After the disc space is prepared, one or more implants are inserted between the adjacent vertebrae in an effort to restore the natural spacing and alignment between the vertebrae, so as to relieve the compression, irritation or pressure on the spinal nerve or nerves and, thereby, eliminate or significantly reduce the pain that the patient is experiencing. Typically, one or more implants are used together with substances that encourage bone ingrowth to facilitate fusion between adjacent vertebrae and achieve immobilization of adjacent bones. Surgeons insert these intervertebral devices to adjunctively facilitate bone fusion in between and into the contiguous involved vertebrae. This fusion creates a new solid bone mass and provides weight bearing support between adjacent vertebral bodies which acts to hold the spinal segment at an appropriate biomechanically restored height as well as to stop motion in a segment of the spine and alleviate pain.

In anterior cervical discectomy and fusion surgery, spinal fusion is achieved in the cervical spine by inserting an implant such as a cage and graft material to encourage bone ingrowth directly into the disc space between adjacent vertebrae. The surgical approach for anterior cervical fusion is from the front of the patient, anterior to the spinal column. A small incision is made in the lower front of the neck, the underlying musculature is dissected and the esophagus and trachea are retracted to expose the front of the cervical spine. Targeted intervertebral discs are removed at the levels to be decompressed. Rongeurs may be employed to remove any remaining bone and disc material. The cage and bone graft material are inserted into the disc space.

In the typical procedure described above, the adjacent vertebrae must be distracted apart by a substantial amount in order to allow the surgeon to advance the implant with relatively little resistance along the delivery path. Also, the surgeon must typically release the implant at least once as the implant is being delivered along the delivery path and align and position the implant at the target position of implantation, typically in the anterior aspect of the disc space. Once positioned, the interbody spacer is secured to the adjacent vertebrae with one or more bone screws. The implant includes apertures formed at one end for passing one or more bone screws at an upward angle into the first adjacent vertebral body and one or more bone screws at a downward angle into the second adjacent vertebral body.

Over time, the interface between the screws and the bone may present some problems of stability. Due to the anatomical structure of the spine and the extreme anatomical forces that are brought to bear on the skeleton and transmitted to the vertebral bodies, the screws securing the interbody spacer to the spine may vibrate or toggle out of position. Also, the degeneration of vertebral bone quality may result in the screws loosening or becoming dislodged. As a result, bone screws may move or back out of the vertebral body and implant. Loosened screws may result instability of the joint and lead to increased pain for the patient.

Therefore, there is a need to provide a new and improved interbody spacer that resists fasteners, such as bone screws, from backing out and also from being loosened with respect to the implant before migrating out. Furthermore, there is a need for the implant to withstand anatomical forces and be easily implanted. Also, the screw retaining mechanism must be easily activated by the surgeon. This invention, as described in the detailed description, sets forth an improved interbody spacer that meets these needs.

SUMMARY OF THE INVENTION

According to one aspect of the invention, a method is provided. The method includes the step of providing an interbody spacer including a cage, at least one bone screw and a screw lock. Each bone screw has a head at a proximal end and a threaded shank extending toward a distal end for anchoring into bone. The screw lock is connected to the cage such that the screw lock is capable of rotational movement with respect to the cage. The screw lock has an unlocked position in which the screw lock does not cover the head of the bone screw inside a bone screw aperture formed in the cage permitting passage of the bone screw in or out of the bone screw aperture and a locked position in which at least part of screw lock is above the head of the bone screw to prevent the bone screw from backing out of the bone screw aperture. Rotation of the screw lock moves the screw lock between the unlocked position and the locked position. The method includes the step of placing the interbody spacer between two adjacent vertebrae of a spine. The method includes the step of inserting the at least one bone screw into the cage and into at least one of the two adjacent vertebrae while the screw lock is connected to the cage and in an unlocked position. The method further including the step of rotating the screw lock from the unlocked position to the locked position.

According to another aspect of the invention, an interbody spacer for a spine is provided. The interbody spacer includes a cage having a top surface and a bottom surface interconnected by a sidewall. The cage includes a central opening extending between the top surface and the bottom surface that defines an inner surface. The cage includes at least one bone screw aperture in the sidewall. The cage includes a lock aperture that is sized and configured to receive a screw lock. The interbody spacer includes at least one bone screw disposed inside the at least one bone screw aperture. Each bone screw includes a head at a proximal end and a threaded shank extending toward a distal end for anchoring into bone. The bone screw is configured to secure the interbody spacer between two bony components of the spine. The interbody spacer further includes a screw lock connected to the cage and located inside the lock aperture. The screw lock has an unlocked position in which the screw lock does not cover the head of the bone screw inside the bone screw aperture permitting passage of the bone screw in or out of the bone screw aperture and a locked position in which at least part of the screw lock is above the head of the bone screw to prevent the bone screw from backing out of the bone screw aperture. Rotation of the screw lock moves the screw lock between the unlocked position and the locked position.

According to another aspect of the invention, an interbody spacer for the spine is provided. The interbody spacer includes a cage having a top surface and a bottom surface interconnected by a sidewall. The cage includes a central opening extending between the top surface and the bottom surface defining an inner surface and a longitudinal axis. The cage includes at least one bone screw aperture in the sidewall. The cage includes a lock aperture that is sized and configured to receive a lock. At least one bone screw is disposed inside the at least one bone screw aperture. Each bone screw has a head at a proximal end and a threaded shank extending toward a distal end for anchoring into bone. The at least one bone screw is configured to secure the interbody spacer between two bony components of the spine. The interbody spacer includes a lock connected to the cage such that the lock is capable of rotational movement with respect to the cage. The lock includes a main body connected to a post. The post is located inside the lock aperture. The lock includes an unlocked position in which the main body does not cover the head of the bone screw inside the bone screw aperture permitting passage of the bone screw in or out of the bone screw aperture and a locked position in which at least part of the main body is above the head of the bone screw to prevent the bone screw from backing out of the bone screw aperture. Rotation of the lock moves the lock between the unlocked position and the locked position. The main body has a cross-section taken perpendicular to the longitudinal axis of the lock. The cross-section has a length and a width. The length is longer than the width. The main body has two oppositely disposed sides along the length interconnected by two oppositely disposed ends along the width. When in the unlocked position, the length is orientated along the longitudinal axis of the cage. At least one of the two sides is curved inwardly to create a concave side facing the at least one bone screw aperture.

BRIEF DESCRIPTION OF THE DRAWINGS

FIG. 16 is a side elevational view of a screw lock of a lock assembly according to the present invention.

FIG. 17 is a cross-sectional view taken along line 17-17 of FIG. 16 of a screw lock of a lock assembly according to the present invention.

FIG. 18 is a cross-sectional view taken along line 18-18 of FIG. 16 of a screw lock of a lock assembly according to the present invention

DETAILED DESCRIPTION OF THE INVENTION

Figure 6:
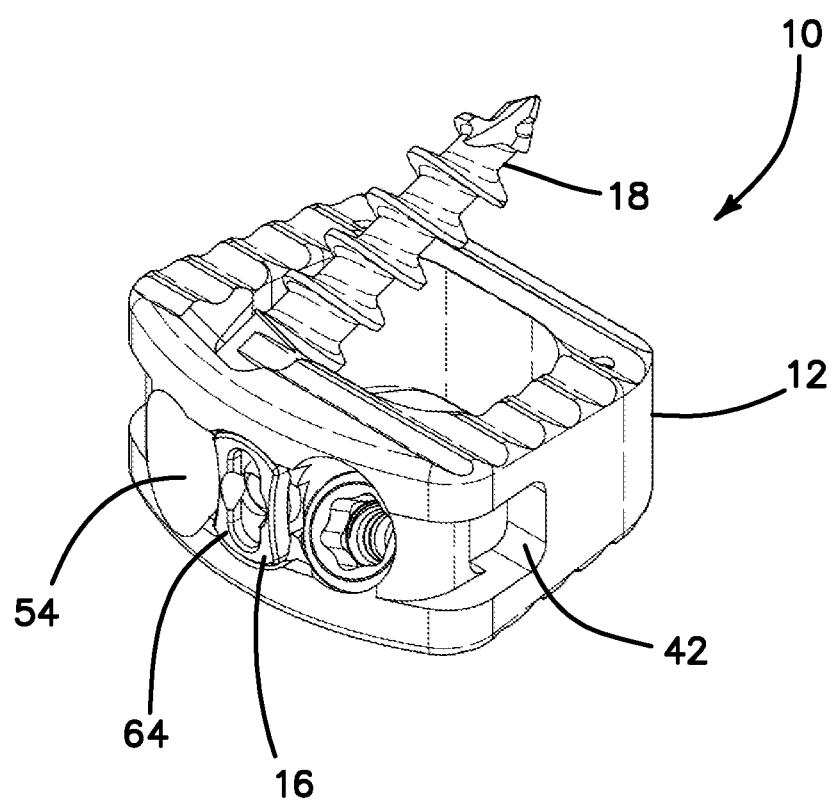
FIG. 6 is a top perspective view of an interbody spacer in an unlocked configuration according to the present invention.
Figure 7:
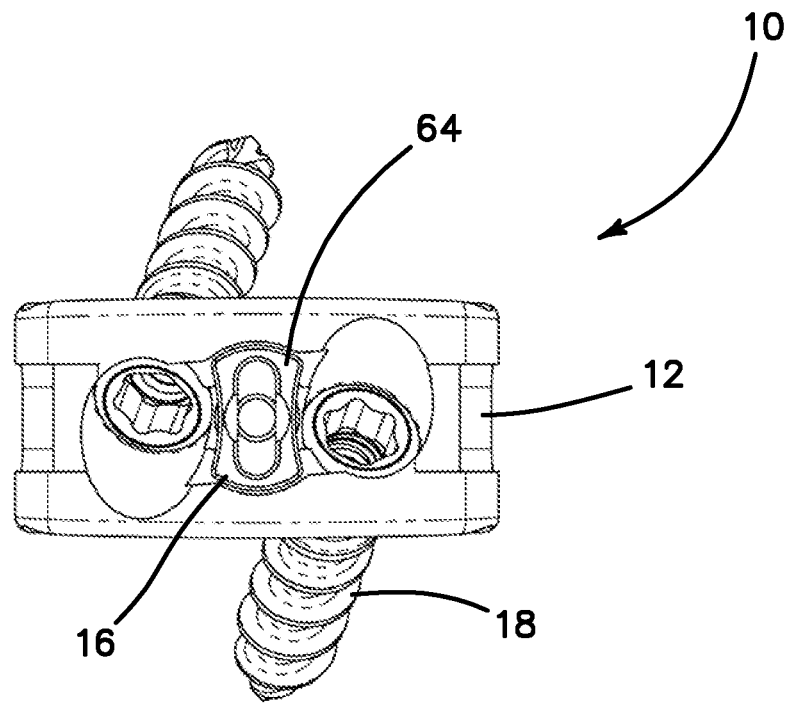
FIG. 7 is a front elevational view of an interbody spacer in an unlocked configuration according to the present invention.
Figure 8:
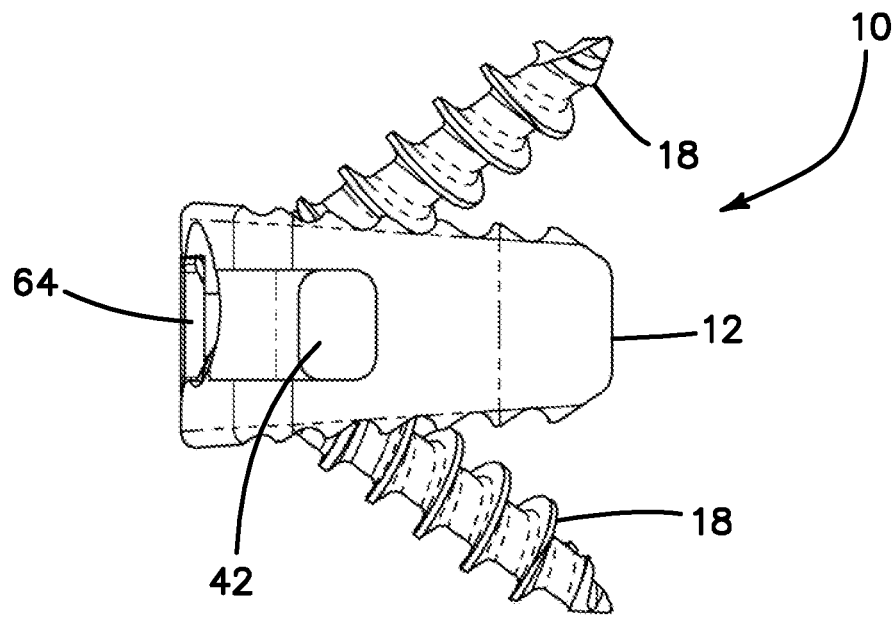
FIG. 8 is a side elevational view of an interbody spacer in an unlocked configuration according to the present invention.
Figure 9:
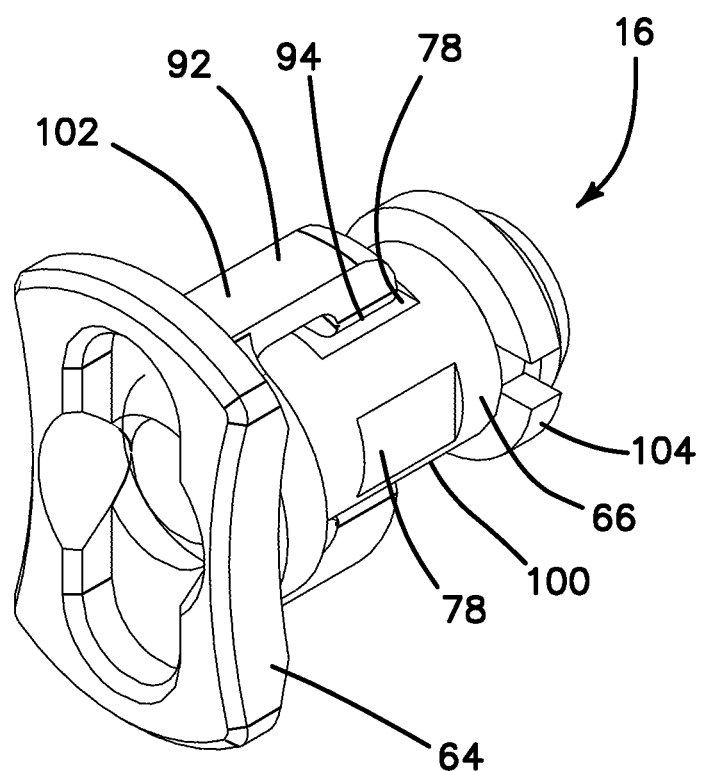
FIG. 9 is a top perspective view of a lock assembly according to the present invention.
Figure 10:
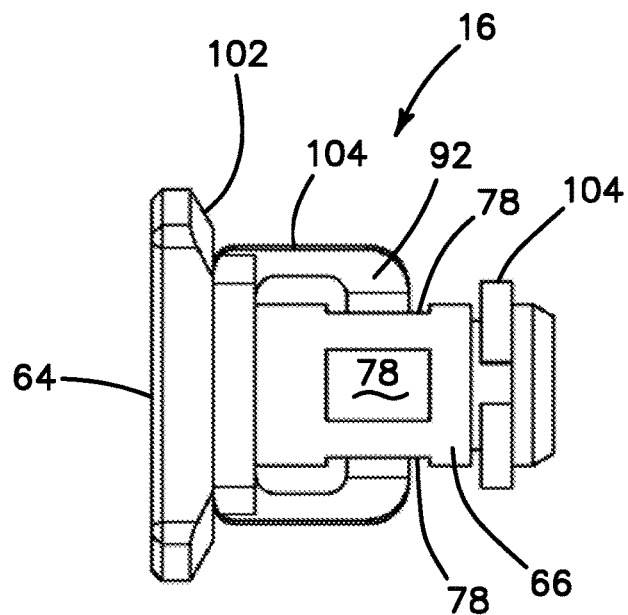
FIG. 10 is a side view of a lock assembly according to the present invention.
Figure 11:
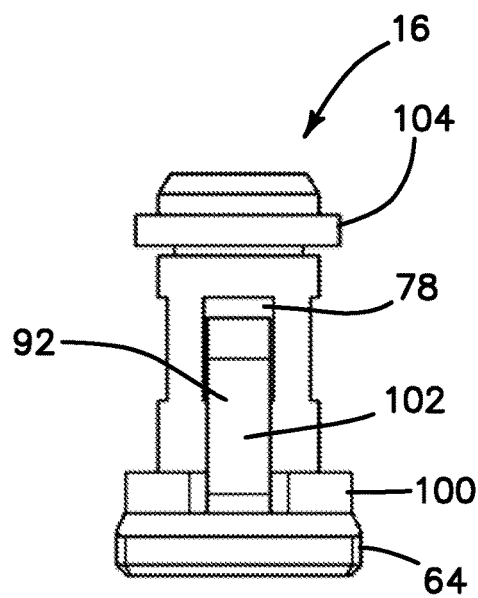
FIG. 11 is a top planar view of a lock assembly according to the present invention.
Figure 12:
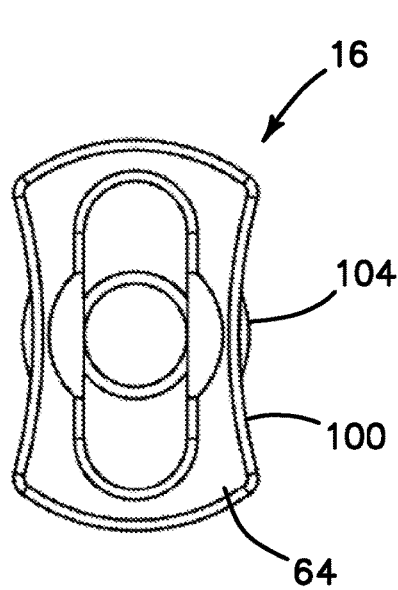
FIG. 12 is a front elevational view of a lock assembly according to the present invention.
Figure 13:
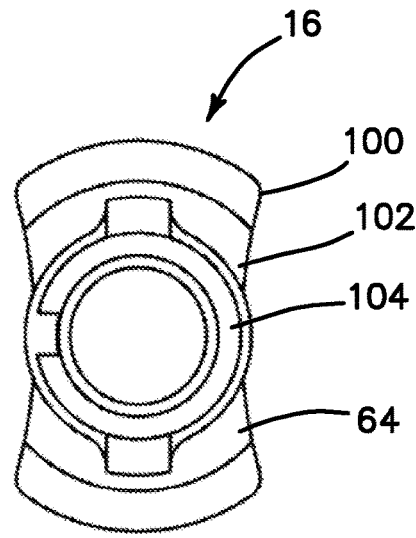
FIG. 13 is a rear elevational view of a lock assembly according to the present invention.
Figure 14:
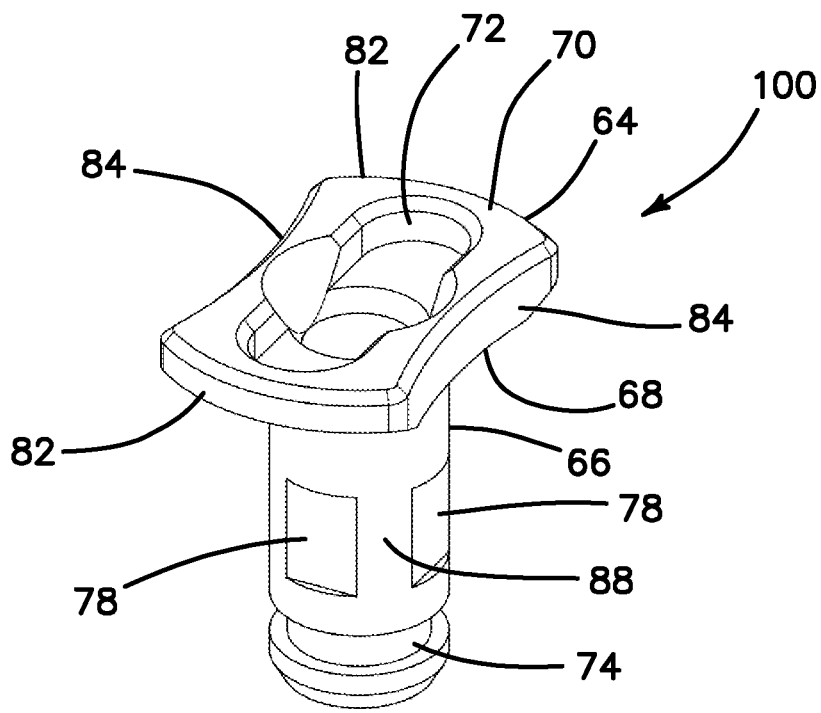
FIG. 14 is a top perspective view of a screw lock of a lock assembly according to the present invention.
Figure 15:
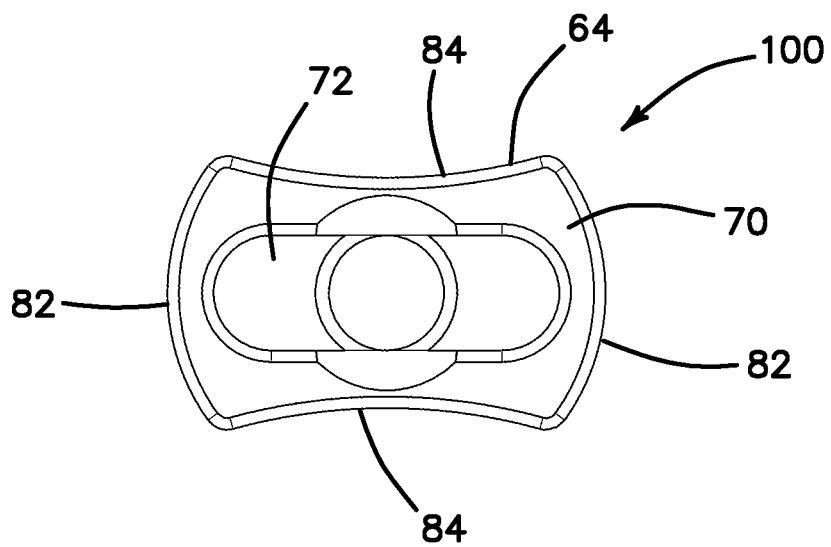
FIG. 15 is a front elevational view of a screw lock of a lock assembly according to the present invention.

FIGS. 1-8 depict an interbody spacer 10 according to one variation of the invention that may be used to stabilize or fuse vertebral bodies in the cervical or other region of the spine. The interbody spacer 10 comprises a cage 12, at least one lock assembly 16, and bone screws 18. The figures depict an interbody spacer 10 having two bone screws 18 and one lock assembly 16 located between the two bone screws 18. The lock assembly 16 is connected to the cage 12 in a manner that permits rotational movement of part of the lock assembly 16 about its longitudinal axis relative to the cage 12. Bone screws 18 are inserted into the cage 12 and when positioned into bone, part of the lock assembly 16 is rotated from an unlocked configuration in which part of each lock assembly 16 does not cover the one or more bone screw 18 to a locked configuration in which part of each lock assembly 16 covers the one or more bone screw 18. In the locked configuration, the at least one lock assembly 16 prevents the backing out of the at least one bone screw 18 with respect to the cage 12. FIGS. 1-5 illustrate the lock assembly 16 in the locked configuration and FIGS. 6-8 show the lock assembly 16 in the unlocked configuration. The figures show two bone screws 18 being covered by one lock assembly 16; however, the invention is not so limited and other arrangements of lock assemblies 16 and bone screws 18 are within the spirit and scope of the present invention. For example, two lock assemblies 16 may be employed to cover two bone screws 18. The bone screws 18 are configured and angled relative to the cage 12 to anchor the interbody spacer 10 between two bony components of the spine. Optional radiographic markers are embedded within the cage 12.

Turning now to FIGS. 9-13, the lock assembly 16 will now be described in greater detail. The lock assembly 16 includes a screw lock 100, a timing lock 102 and a retaining ring 104. The screw lock 100 and the timing lock 102 are connected to the cage 12. The screw lock 100 is coupled to the cage 12 via the retaining ring 104 such that the screw lock 100 is rotationally movable about its longitudinal axis with respect to the cage 12. The timing lock 102 is fixed with respect to the cage 12.

Turning now to FIGS. 14-18, the screw lock 100 will be described in greater detail. The screw lock 100 includes a main body 64 connected to a lock post 66. The main body 64 includes a bottom surface 68 and a top surface 70. The lock post 66 extends from a bottom surface 68 of a main body 64 along the longitudinal axis of the screw lock 100 to a distal end of the screw lock 100. The post 66 is configured to be inserted into a lock aperture 40 of the cage 12 and connected to the cage 12 via the retaining ring 104 such that the screw lock 100 can rotate relative to the cage 12 about the longitudinal axis of the post 66. Whereas the post 66 is inserted into the cage 12, the main body 64 of the screw lock 100 resides above the sidewall 28 of the cage 12 next to at least one bone screw aperture 54 in the location of a lock recess 38 if a lock recess 38 is provided in the cage 12 preferably such that the main body 64 of the screw lock assembly 16 does not substantially extend beyond the outer profile of the cage 12 maintaining an anterior surface 30 having a smooth low profile. The top surface 70 of the screw lock 100 includes a socket 72. The socket 72 is configured to receive an instrument such as a driver having a complementary shaped tip for engaging and rotating the screw lock 100 between an unlocked position and a locked position. The lock post 66 extends downwardly from the bottom surface 68 of the main body 64. The lock post 66 has a retaining ring receiving location 74. The retaining ring receiving location 74 is a circumferential channel extending around the lock post 66 and having a perimeter diameter that is smaller than the surrounding diameter of the lock post 66 as can be seen in FIG. 18. The retaining ring receiving location 74 is sized and configured to receive and seat at least a portion of the retaining ring 104 such that the retaining ring 104 extends radially outwardly beyond outer diameter of the post 66. At a location proximal to the retaining ring receiving location 74, the lock post 66 is faceted and, in a cross-section perpendicular to the longitudinal axis, has a reduced area and a polygonal shape that can be described as having two oppositely disposed parallel sides 78 that are interconnected to two oppositely disposed parallel sides 78 by beveled corners 80 for a total of eight facets that are all substantially parallel to the longitudinal axis as can be seen in FIG. 17. The beveled corners 80 are rounded being a part of the outer surface of the lock post 66. The beveled corners are oppositely located and the cross-section has a generally square or rectangular geometric shape with the beveled corners 80 having a concave outer surface that matches the curvature of the neck 76.

With respect to the main body 64, the top surface 70 and the bottom surface 68 of the main body 64 are interconnected by two ends 82 and two sides 84. The two ends 82 are opposite from each other and have a generally convex surface. The two sides 84 are opposite from each other and have a generally concave surface. Together, the two ends 82 and the two sides 84 define an elongate, rectangular-like shape when viewed from the top with the two sides 84 having a length that is greater than the length of the two ends 82. Although a rectangular or elongate shape is shown in the figures, the main body 64 can have any other suitable shape such as elliptical or circular.

Figure 19:
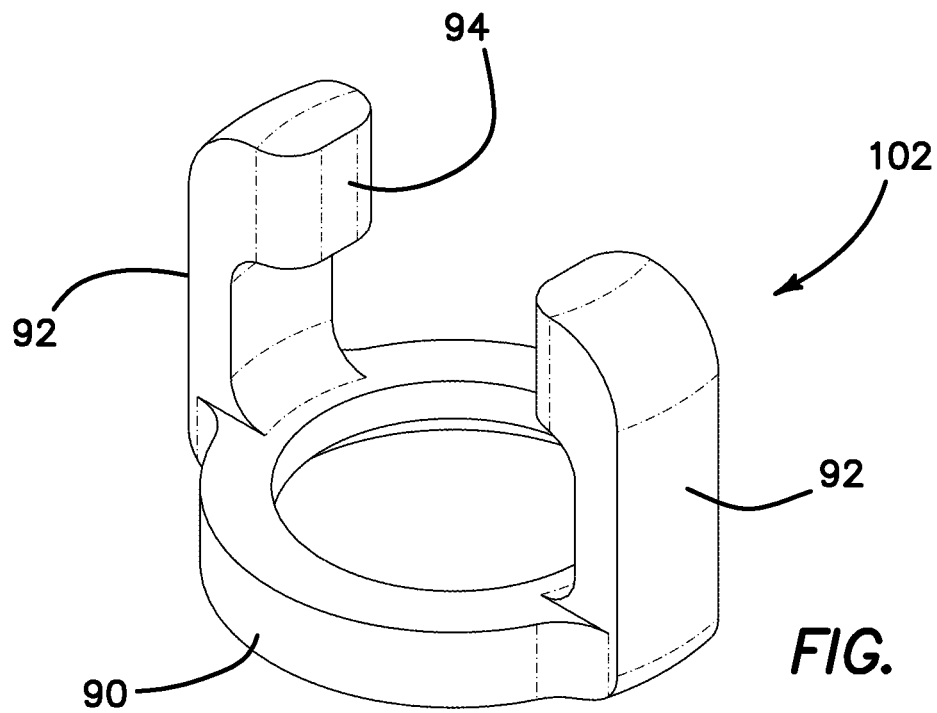
FIG. 19 is a top perspective view of a timing lock of a lock assembly according to the present invention.
Figure 20:
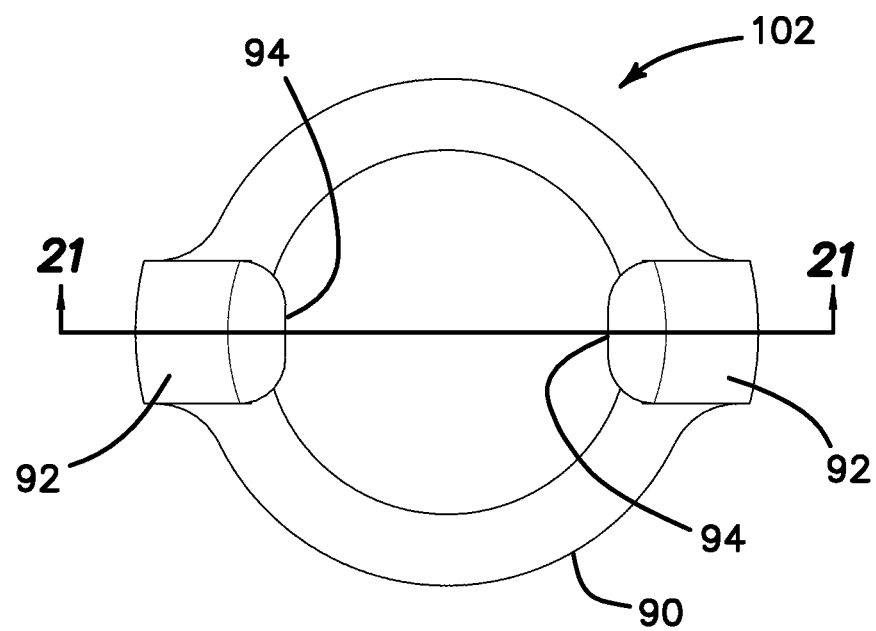
FIG. 20 is a top planar view of a timing lock of a lock assembly according to the present invention.
Figure 21:
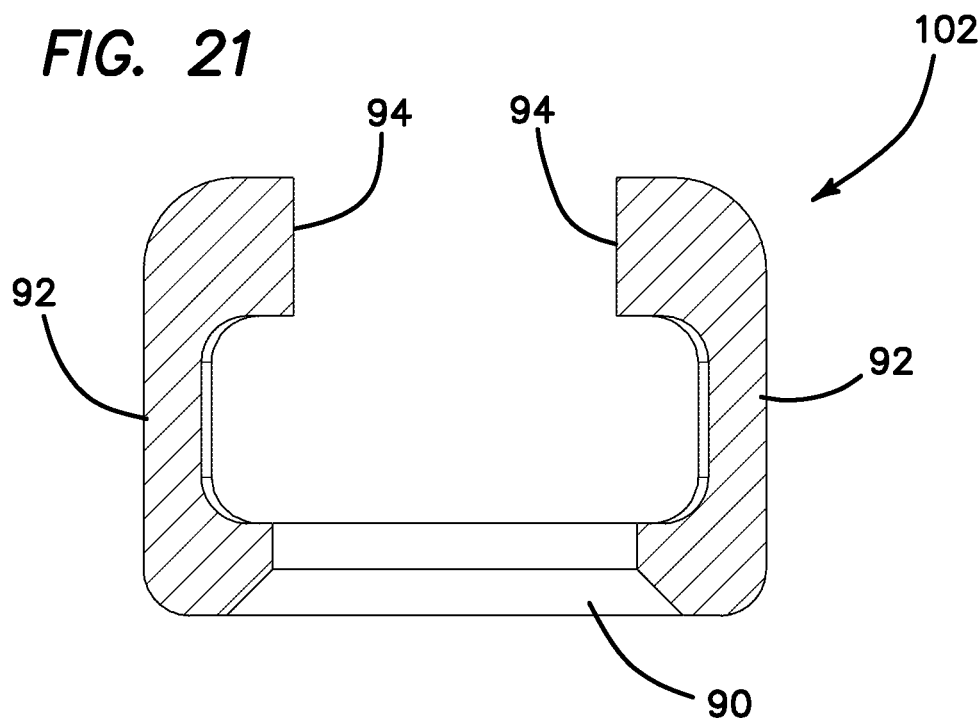
FIG. 21 is a cross-sectional view taken along line 21-21 of FIG. 20 of a timing lock of a lock assembly according to the present invention.

Turning now to FIGS. 19-21, the timing lock 102 will now be described in greater detail. The timing lock 102 includes a circular base 90 with two upstanding prongs 92. The prongs 92 extend upwardly from the base 90 opposite from each other. Two prongs 92 are provided and their distal ends project slightly toward the longitudinal axis and include two oppositely disposed prong faces 94. The prong faces 94 are substantially parallel to the longitudinal axis. The two prong faces 94 are sized and configured to simultaneously engage two oppositely disposed sides 78 of the post 66. Each prong face 94 is shaped and sized to be substantially equal or less than in shape and size as each side 78 of the post 66. The circular base 90 defines an opening that is sized and configured to receive the post 66 of the screw lock 100. When the distal end of the screw lock 100 is inserted into the opening in the base 90 of the timing lock 102 and moved distally such that the proximal end of the timing lock 102, and in particular, the proximal end of the circular base 90 contacts the bottom surface 68 of the main body 64, the prongs 92 of the timing lock 102 are in position such that the prong faces 94 engage, contact, and/or nearly engage the sides 78 of the post 66 in a manner that permits rotation of the screw lock 100 relative to the timing lock 102. With rotation of the screw lock 100 relative to the timing lock 102, the prong faces 94 will move from being in juxtaposition with or in contact with the sides of the post 66 to being in contact with the beveled corners 80. Since the diagonal of the cross-section of the post 66 is longer in length than the distance between opposite sides 78, a force will be required to move past the engagement with the beveled corners 80. Such force applied via rotation of the screw lock 100 will flex the prongs 92 slightly outwardly from the longitudinal axis splaying them outwardly permitting completion of rotation to a position wherein the prong faces 94 are again directly opposite to two sides 78 of the post 66. Such rotation of the screw lock 100 provides a tactile sensation to the user wherein the user feels a resistance upon contact with the beveled corners 80 requiring increased force to continue with the rotation of the screw lock 100. The user will then feel a release or relaxation of the resistance and an ease in the rotation as the prongs 92 spring back to their normal state in a position opposite the sides 78 of the post 66 to thereby provide a metered rotation as will be described in greater detail below.

Figure 22:
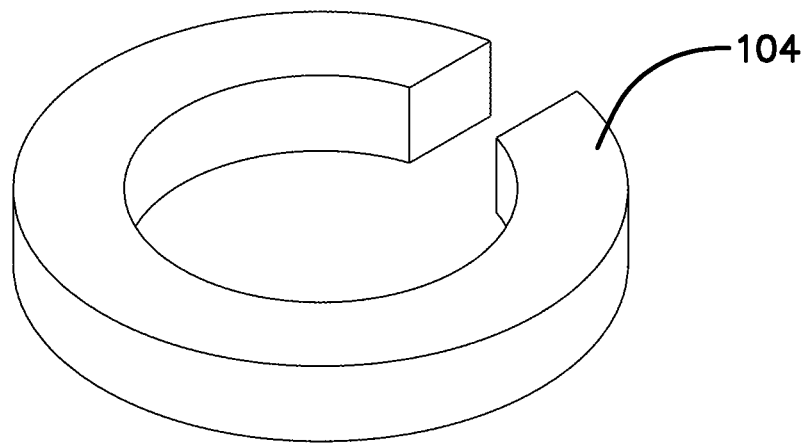
FIG. 22 is a top perspective view of a retaining ring of a lock assembly according to the present invention.

Turning now to FIG. 22, the retaining ring 104 will now be described in greater detail. The retaining ring 104 is a split ring made of metal and defining a central opening. The central opening is sized and configured to receive the post 66 and to seat the retaining ring 104 in the retaining ring receiving location 74. The retaining ring 104 can flex into a larger diametrical size to be located over the post 66 where it springs back into a neutral unstressed diameter. When seated in the retaining ring receiving location 74, the retaining ring 104 provides a location of increased diameter and serves as a distal stop that abuts the inner surface 46 of the cage 12 and prevents the screw lock 100 from moving proximally out of the cage 12 as will be described in greater detail below.

Turning now to the FIGS. 23-26, the cage 12 will now be described in greater detail. The cage 12 includes a top surface 24 and a bottom surface 26 interconnected by at least one sidewall 28 extending between the top surface 24 and the bottom surface 26 defining a cage height. The cage 12 has a shape that mimics a spinal disc. The sidewall 28 has an anterior surface 30 and a posterior surface 32 interconnected by two side surfaces 34, 36. In one variation, the anterior surface 30 has a larger cage height relative to the posterior surface 32 imparting the cage 12 with a wedge-like configuration having a taper from the anterior surface 30 to the posterior surface 32. This taper is designed to accommodate the natural anatomic relationship between adjacent vertebral bones and maintain the normal lordotic curvature of the spine. The cage 12 has a lordotic angle that is between approximately 5 degrees and 15 degrees. The lordotic angle can be between approximately 5 degrees and 28 degrees. The cage 12 has a cage height of approximately 4-12 mm such as approximately 4 mm, 6 mm, 8 mm, 10 mm and 12 mm. The anterior and posterior surfaces 30, 32 are longer than the side surfaces 34, 36 when measured along a lateral dimension giving the cage 12 an elongate shape when viewed along the longitudinal axis. The lateral dimension of the cage 12 as measured between side surfaces 34, 36 is approximately 10 mm-20 mm and the anterior-to-posterior dimension is approximately 10 mm-20 mm. The intersections of the surfaces 30, 32, 34 and 36 are smooth and rounded giving the cage 12 an overall oval or oblong shape.

Figure 1:
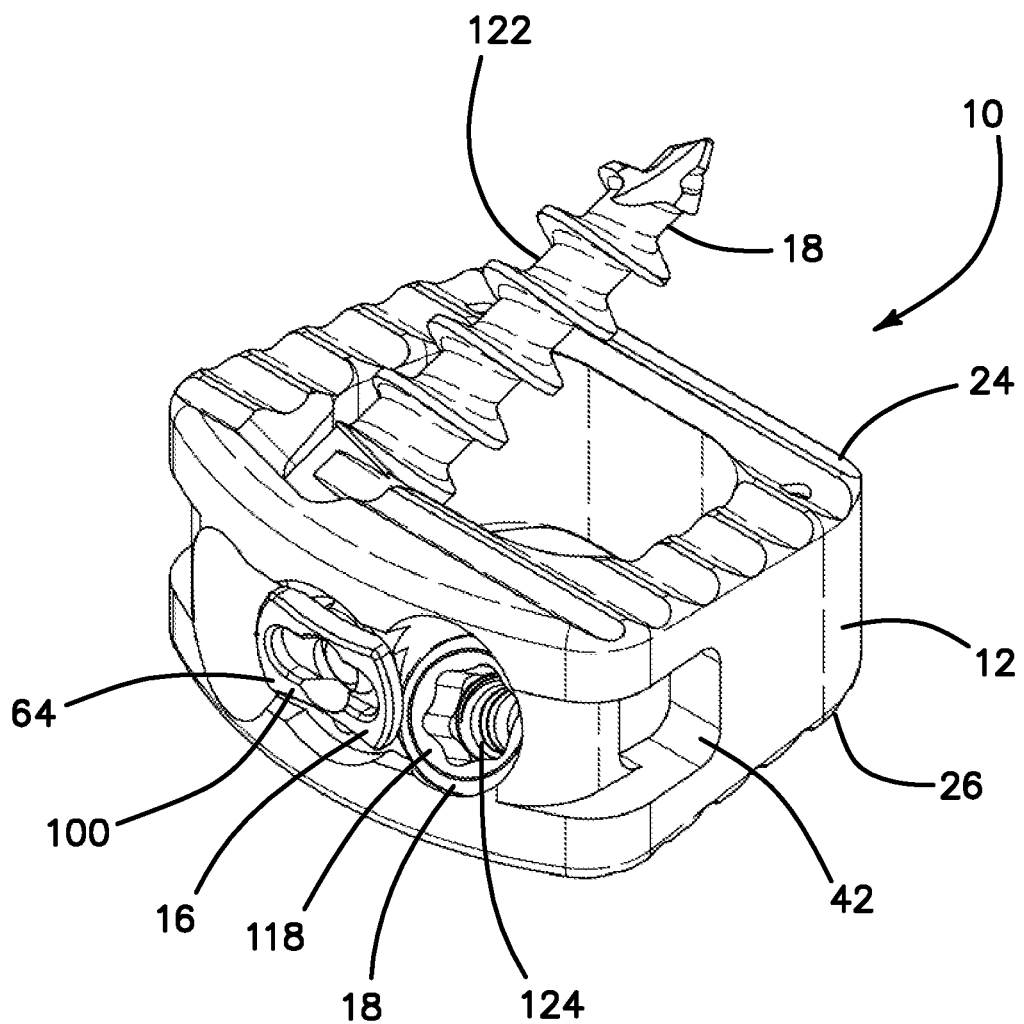
FIG. 1 is a top perspective view of an interbody spacer in a locked configuration according to the present invention.
Figure 2:
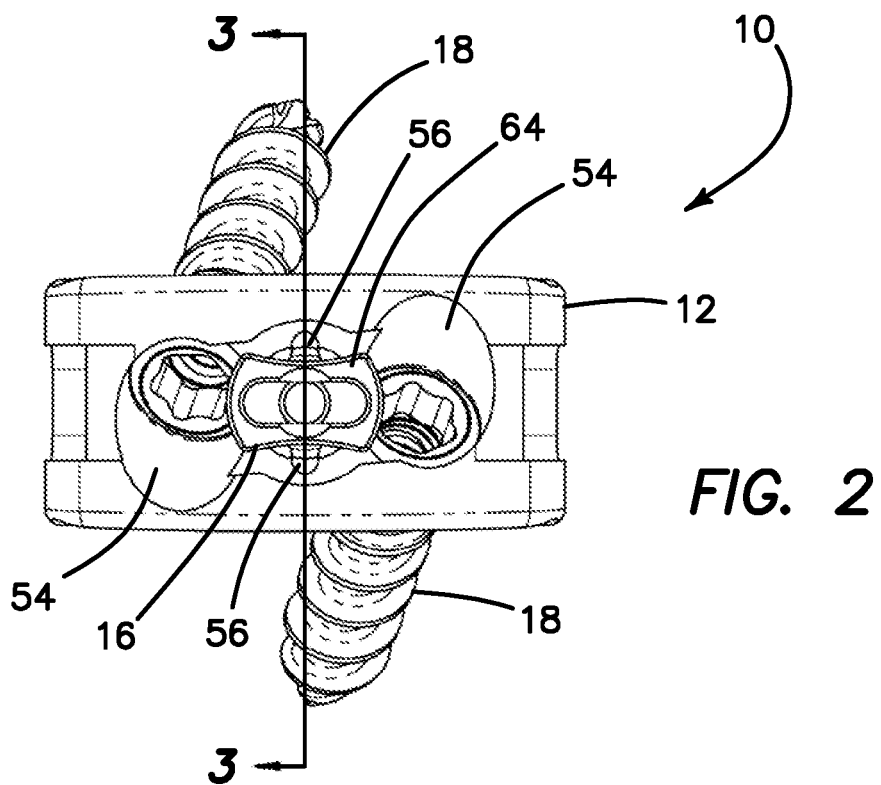
FIG. 2 is a front elevational view of an interbody spacer in a locked configuration according to the present invention.
Figure 3:
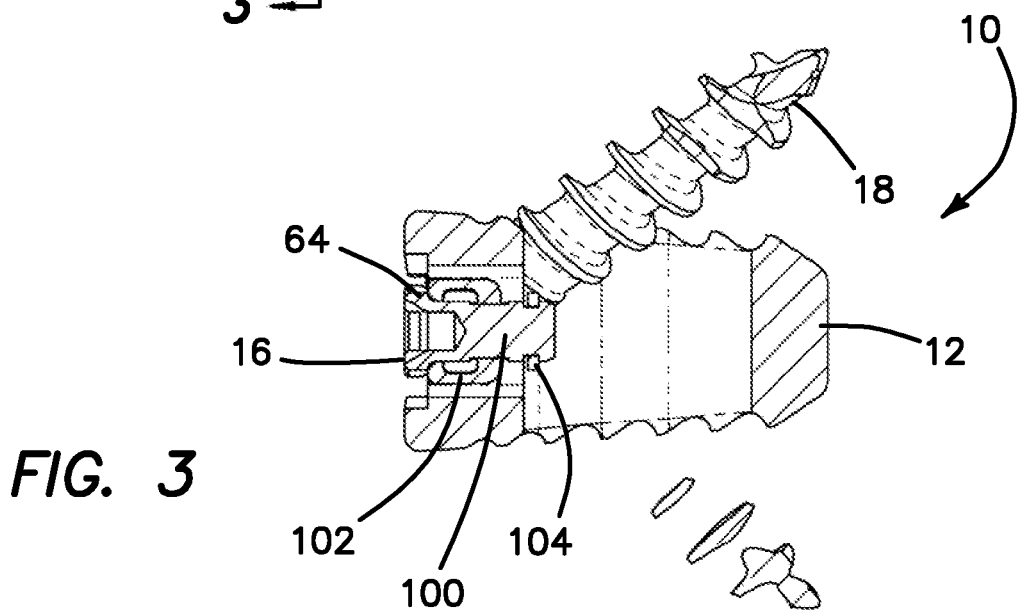
FIG. 3 is a cross-sectional view taken along line 3-3 of FIG. 2 of an interbody spacer in a locked configuration according to the present invention.
Figure 4:
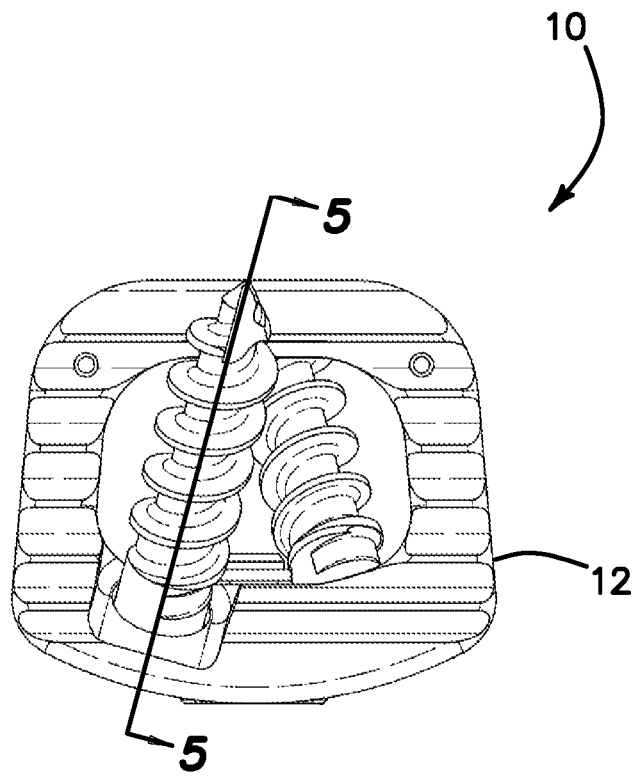
FIG. 4 is a top planar view of an interbody spacer in a locked configuration according to the present invention.
Figure 5:
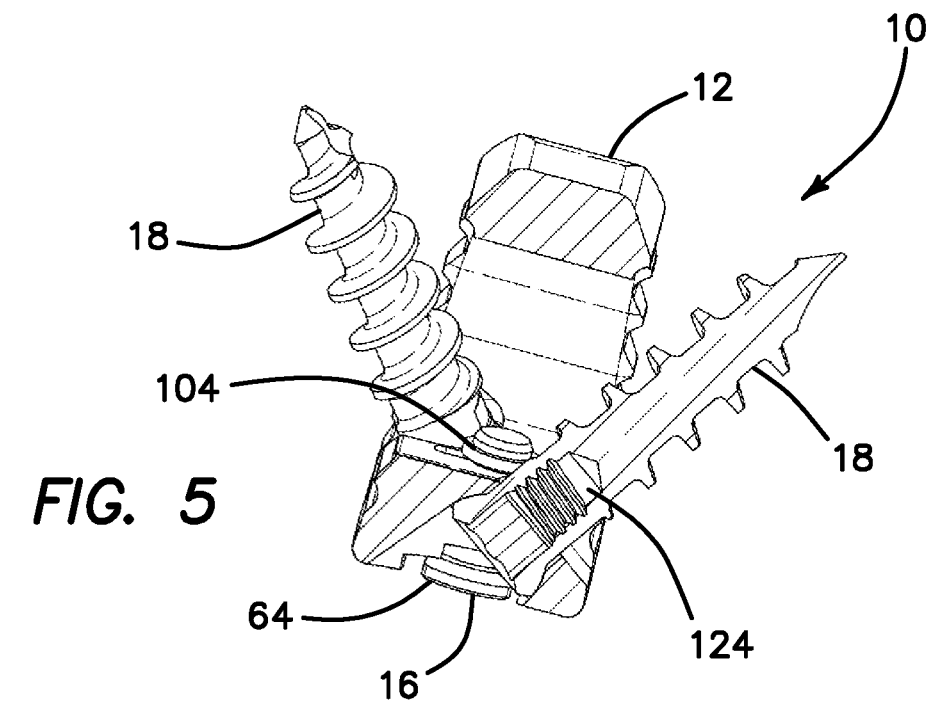
FIG. 5 is a cross-sectional view taken along line 5-5 of FIG. 4 of an interbody spacer in a locked configuration according to the present invention.
Figure 23:
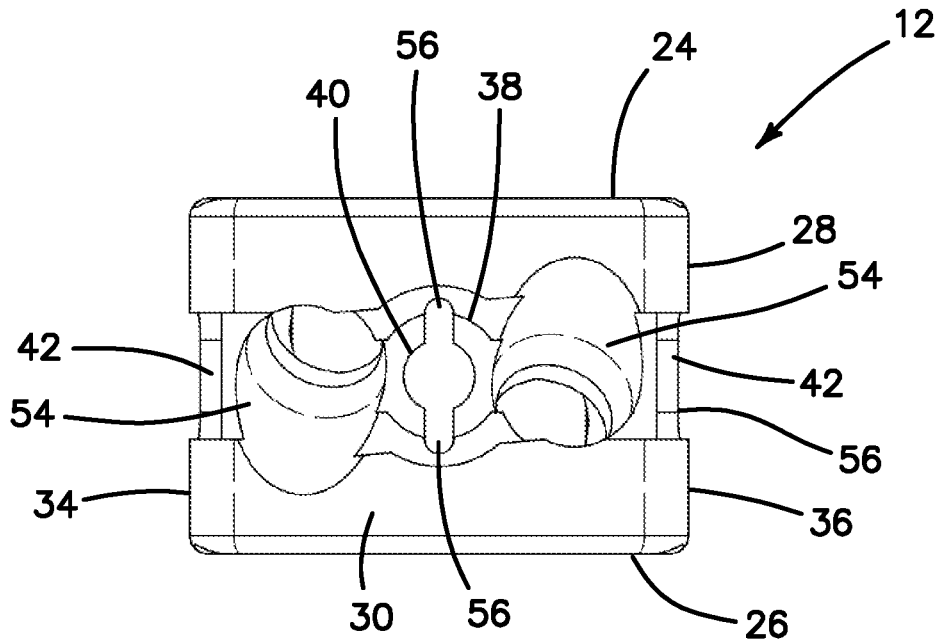
FIG. 23 is a front elevational view of a cage according to the present invention.
Figure 24:
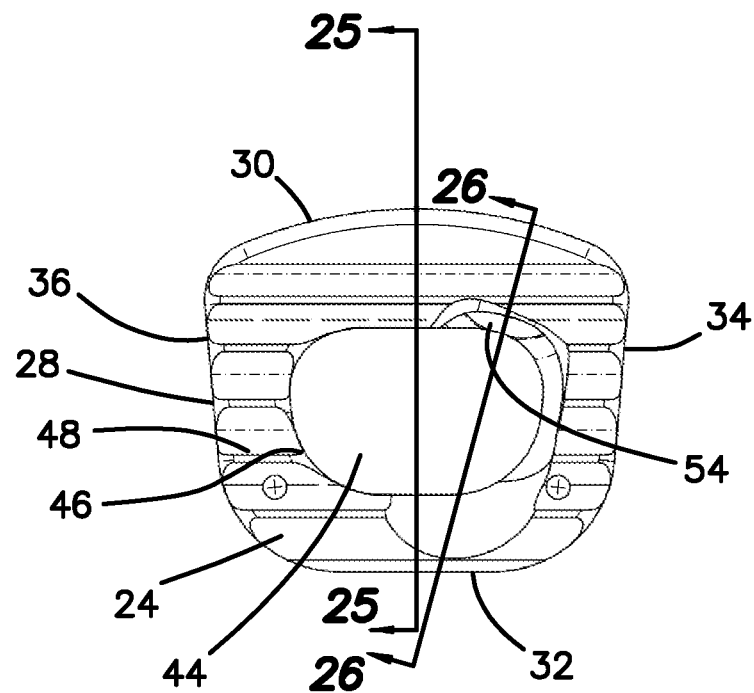
FIG. 24 is a top planar view of a cage according to the present invention.
Figure 25:
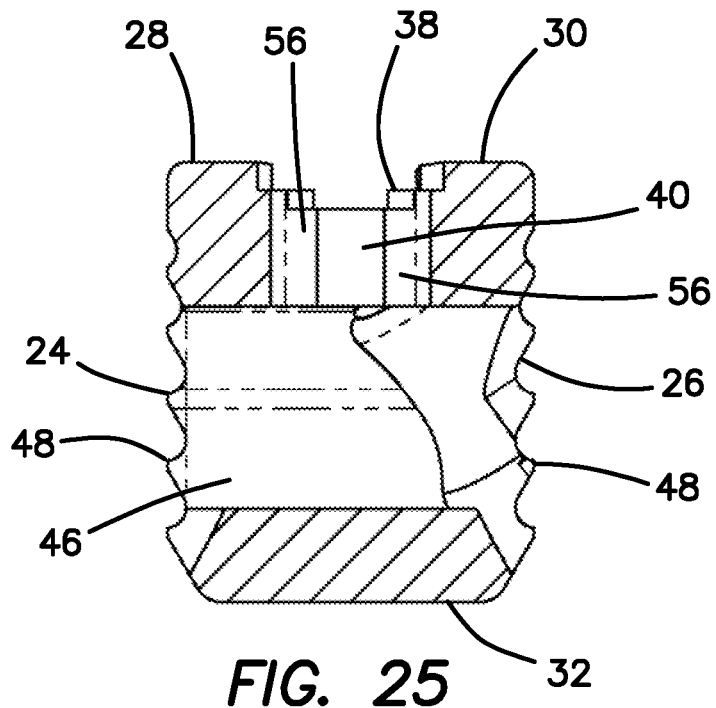
FIG. 25 is a cross-sectional view taken along line 25-25 of FIG. 24 of a cage according to the present invention.
Figure 26:
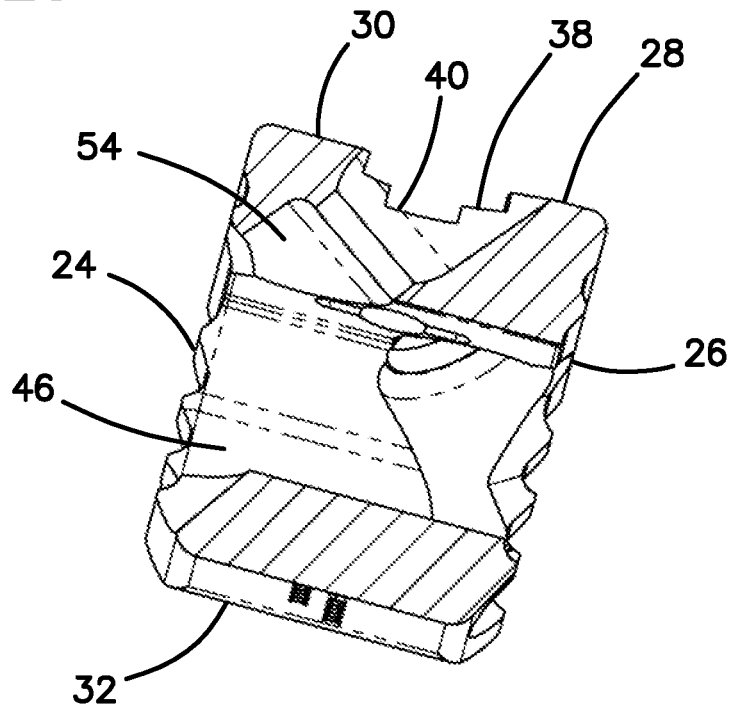
FIG. 26 is a cross-sectional view taken along line 26-26 of FIG. 24 of a cage according to the present invention.

The anterior surface 30 of the cage 12 includes a lock recess 38. The lock recess 38 is sized and configured to conform to and to receive the at least one lock assembly 16. When the at least one lock assembly 16 is attached to the cage 12, the lock assembly 16 is recessed such that the main body 64 of the screw lock 100 does not significantly protrude or extend outwardly from the anterior surface 30. In one variation, the depth of the lock recess 38 substantially equals the thickness of the main body 64 of the screw lock 100 such that the top surface 70 of the main body 64 is substantially flush with the anterior surface 30 when attached to the cage 12. The cage 12 further includes a lock aperture 40 having a longitudinal axis. In one variation, the lock aperture 40 is formed in the anterior surface 30 of the cage 12 such that the longitudinal axis of the lock aperture 40 is substantially perpendicular to the anterior surface 30. In one variation, the lock aperture 40 is located within the perimeter of a lock recess 38. In one variation, the cage 12 does not include any lock recesses 38. In such a variation, the lock aperture 40 may be sized and shaped to recess the lock assembly 16 when it is in the locked configuration. The lock aperture 40 is sized and configured to receive at least a portion of the lock assembly 16. In particular the lock aperture 40 includes a central bore to receive the post 66 of the screw lock 100 and oppositely disposed side apertures 56 as can be seen in FIGS. 2 and 23. The side apertures 56 are sized and configured to receive the prongs 92 of the timing lock 102 and fix the timing lock 102 with respect to the cage 12 to prevent the timing lock 102 from rotating or moving with respect to the cage 12. One or more lock recesses 38 may be formed to accommodate the one or more lock assembly 16. Also, a single lock recess 38 may be large enough to accommodate more than one lock aperture 40 and lock assembly 16 received therein. As shown in the figures, one lock aperture 40 is formed to accommodate one lock assembly 16 received therein. One or more lock recesses and accompanying lock apertures may be formed to accommodate the one or more lock assembly 16 and their position on the cage 12.

The side surfaces 34, 36 of the cage 12 each include instrument notches 42 which serve as tool receiving recesses that are sized and configured to receive oppositely disposed distal prongs of an insertion instrument used for delivering, implanting and removing the interbody spacer 10. The instrument notches 42 are also visible in FIG. 27. The instrument notches 42 are formed laterally oppositely from each other near the lateral axis of the cage 12. The instrument notches 42 may include a ramped surface such that the prongs of an insertion instrument do not unduly extend laterally outwardly from the side surfaces 34, 36.

The top surface 24 or superior surface of the cage 12 is configured for engaging a lower endplate of a first vertebral bone and the bottom surface 26 or inferior surface of the cage 12 is configured for engaging an upper endplate of an adjacent second vertebral bone of the spine. The top and bottom surfaces 24, 26 are spaced apart with the sidewall 28 extending therebetween. The top and bottom surfaces 24, 26 define a longitudinal axis extending substantially normal to the top and bottom surfaces 24, 26. It is understood that the longitudinal axis is not precisely normal to the top and bottom surfaces 24, 26 due to the narrowing height and lordotic angle of the cage 12 from the anterior surface 30 to the posterior surface 32. The longitudinal axis of the cage 12 is approximately parallel to or substantially coaxial with the longitudinal direction of the spine when the interbody spacer 10 is implanted. Extending between the top surface 24 and the bottom surface 26 is a central cage opening 44 having an opening at the top surface 24 and extending to an opening at the bottom surface 26 and, thereby, defining an inner surface 46 and central lumen of the cage 12. The central cage opening 44 reduces the weight of the cage 12 and permits bone ingrowth to take place into and through the cage 12. A family of bone graft materials, such as autograft, bone morphogenic protein (BMP), bone marrow aspirate, concentrate, stem cells and the like, may be placed inside the central cage opening 44 to promote bone growth into the cage 12. A plurality of ridges 48 are formed on the top surface 24 and the bottom surface 26. The ridges 48 have pointed peaks to engage and increase the purchase on the endplates of adjacent vertebra. The ridges 48 may further be angled with respect to the top and bottom surfaces 24, 26 such that the ridges 48 help to hold and prevent migration of the cage 12 relative to the adjacent vertebrae when implanted within the intervertebral space. The top surface 24 and/or the bottom surface 26 of the cage 12 may include one or more radiographic pin holes for receiving radiographic markers.

The cage 12 further includes one or more bone screw apertures 54 formed in the sidewall 28 configured to direct bone screws 18 upwardly and/or downwardly to engage adjacent vertebrae. In the variation shown in the figures, two bone screw apertures 54 are formed in the anterior surface 30 intersecting with the at least one lock recess 38 and extend transversely across the sidewall 28 and open into the inner surface 46 and top surface 24 of the cage 12. One or more bone screw apertures 54 are angled toward the top surface 24 such that bone screws 18 inserted therein are directed into the lower endplate of the adjacent upper vertebra. In the figures, one bone screw aperture 54 is shown angled upwardly toward the upper vertebral body. One or more bone screw apertures 54 are angled toward the bottom surface 26 such that bone screws 18 inserted therein are directed into the upper endplate of the adjacent lower vertebra. In the figures, one bone screw aperture 54 is shown angled downwardly toward the lower vertebral body. Each bone screw aperture 54 may include an interior ledge for contact with the head of the bone screw 18. The interior ledge divides the bone screw aperture 54 into a bone screw shaft receiving portion and a bone screw head receiving portion. The inner diameter of the head receiving portion is larger than the inner diameter of the shaft receiving portion to accommodate the relatively larger head of the bone screw 18 and to permit it to angulate substantially polyaxially. The angulation of the bone screw aperture 54 results in a fluted entry. All of the bone screw apertures 54 are formed near lock apertures 40 such that when a lock assembly 16 is installed and rotated into a locked configuration, it covers at least one of the bone screws 18 inserted therein to prevent it from backing out of the cage 12. A lock aperture 40 is located between two bone screw apertures 54.

With reference back to FIG. 1, the bone screw 18 will now be described in greater detail. The bone screws 18 used with the cage are exemplary orthopedic fasteners that are preferably used with the interbody spacer 10 of the present invention although other types of fasteners may be employed. The bone screw 18 includes a screw head 118, neck and threaded shank 122. The head 118 is bulbous having a larger lateral dimension than the threaded shank 122. Also, the outer surface of the head 118 is curved, spherical in shape or partially spherical or a frustum or frusta of a sphere having a region of a sphere delimited by one plane parallel to a plane containing a diameter or having a region of a sphere delimited by two planes which in one variation may be parallel to each other. The proximal plane of the frusta-spherical head 118 includes an opening that serves as an instrument recess or socket 124 configured to engage a complementary tip of a surgical tool for driving the bone screw into bone. A substantially hexagonal, daisy-shaped recess 124 is shown; however, the recess 124 can be of any shape that allows a surgical tool to drive the bone screws 18 into the vertebral column. The head 118 of the bone screw 18 corresponds to the shape of the bone screw apertures 54 in the cage 12. The bone screws 18 are configured to allow polyaxial, variable angle or fixed angled orientation with respect to the cage 12 while disposed inside the bone screw apertures 54. The angulation of the bone screws 18 with respect to the cage 12 allows a desired angle or orientation with respect to the cage 12 and adjacent vertebral bodies to be achieved to anchor the cage 12 to the vertebrae. The bone screws 18 are preferably self-tapping and configured for insertion into bony material, however, other screws requiring holes to be drilled or pre-tapped can also be employed.

The cage 12 is typically made of a polymer such as polyether ether ketone (PEEK) which is a thermoplastic polymer that has been widely accepted for use in the manufacture of medical implants. PEEK has excellent mechanical, chemical resistance and biocompatible properties and has been finding increased use in spinal fusion devices as it mimics the stiffness of real bone. While many medical implants are made entirely of PEEK, many implants have both PEEK components and non-PEEK components such as stainless steel and titanium. The cage 12 may also be made of metal. The bone screws 18 and lock assembly 16 are made of metal such as surgical stainless steel and titanium.

Figure 27:
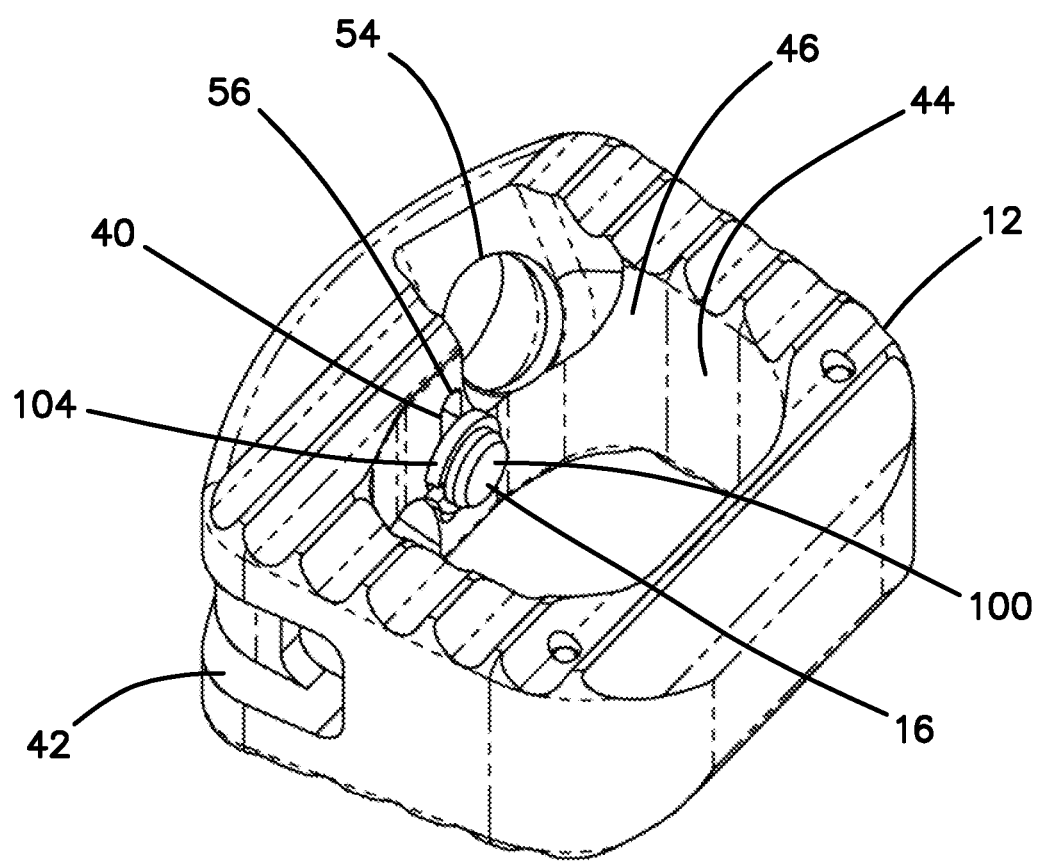
FIG. 27 is a top perspective view of a cage and lock assembly according to the present invention.

The interbody spacer 10 is assembled by inserting the post 66 of the screw lock 100 into the aperture of the timing lock 102 until the two oppositely disposed prong faces 94 are in juxtaposition with two oppositely disposed flats 78. The combination of the screw lock 100 and the timing lock 102 is then inserted into the lock aperture 40 from the anterior surface 30 of the cage 12. An instrument such as a lock driver can be inserted into the socket 72 of the screw lock 100 to assist in the insertion of the screw lock 100 and the timing lock 102 into the lock aperture 40. The timing lock 102 is aligned with respect to the side apertures 56 and the timing lock 102 and the screw lock 100 are inserted into the lock aperture 40 such that the main body 64 is resident above the sidewall 28 within the lock recess 38 yet substantially flush with respect to the anterior surface 30 for a low-profile arrangement. When fully inserted, the distal end of the screw lock 100 projects into the central cage opening 44 by a distance sufficient to expose the retaining ring receiving location 74 on the post 66 as can be seen in FIG. 27. The retaining ring 104 is diametrically expanded and placed into the retaining ring receiving location 74. With the retaining ring 104 in position, the lock assembly 16 is fully installed. The retaining ring 104 has a diameter that is larger than the diameter of the lock aperture 40 and abuts the inner surface 46 of the cage 12 connecting the lock assembly 16 to the cage 12 and preventing the lock assembly 16 from backing out of the cage 12. Displacement of the lock in the proximal direction is prevented by the retaining ring 104. The lock assembly 16 is connected to the cage 12 in such a manner that the lock is permitted to rotate with respect to the cage 12 between an unlocked configuration and a locked configuration. Bone screws 18 are inserted into the bone screw apertures 54 when the screw lock 100 is in an unlocked position before surgery or in-situ during surgery.

With reference to FIGS. 6-8, the screw lock 100 is shown in an unlocked configuration. When in the unlocked configuration, the screw lock 100 is oriented substantially vertically, parallel to the longitudinal axis of the cage 12. The curved sides 84 of the main body 64 of the lock assembly 16 face the bone screw apertures 54. The curvature of the sides 84 provides clearance for the pathway for the insertion of bone screws 18 and advantageously allows the interbody spacer 10 to be made smaller in the lateral dimension perpendicular to the longitudinal axis of the cage 12. In an unlocked configuration, with the bone screws 18 inserted, one or more side 84 is in juxtaposition with the one or more inserted the bone screws 18. In the variation shown in the figures, the two sides 84 are facing the two bone screws 18. The unlocked configuration permits unhampered insertion and removal of bone screws 18. When inserted, the shape of the bone screw apertures 54 permit the bone screws 18 to angulate polyaxially with respect to the cage 12 for ideal positioning into bone.

With reference to FIGS. 1-5, the screw lock 100 is shown in a locked configuration. When in the locked configuration, the screw lock 100 is oriented substantially horizontally or perpendicular to the longitudinal axis of the cage 12; however, the invention is not so limited and the locks 16 need only be angled away from the vertical orientation parallel to the longitudinal axis to effect a locked configuration in which at least a portion of the main body 64 covers one or more bone screw heads 118 to prevent them from backing out with respect to the cage 12. The distance between the ends 82 of the main body 64 is longer than the distance between the sides 84 of the main body 64. The long length of the main body is moved away from its vertical orientation to cover the bone screw 18. When the lock assembly 16 is rotated from an unlocked configuration toward a locked configuration, the main body 64 of the lock assembly 16 because of its shape will move into the space of the bone screw apertures 54 where the bone screws 18 reside. Rotation of the lock main body 64 continues until at least a portion of the main body 64 covers the head 118 of the bone screw 18 to prevent backing out of the screw 18. The degree of rotation required to prevent the backing out of screws will vary depending upon the angulation of the bone screw 18, the final positioning of the bone screw 18 with respect to the anatomy and the arrangement of the screw lock 100 with respect to the cage 12. As shown in the figures, the screw lock 100 is free to rotate 360 degrees about its axis. In other variations, the screw lock 100 may be restricted to movement of approximately 90 degrees. In the variation shown in the figures, a rotation of the screw lock 100 between approximately 0 and 180 degrees will effect a locked configuration preventing the back out of screws. Rotation of the screw lock 100 between approximately 30 and 150 degrees will cover more of the bone screw and also effect a locked configuration preventing the back out of screws. Advantageously, this wide range permits even a small rotation such as 20 degrees to cover the bone screw 18 and this small rotation can be made in either a clockwise or counterclockwise direction to simultaneously cover two adjacent bone screws 18 with one lock assembly 16. The system also advantageously permits the surgeon to achieve an ideal positioning of the bone screws 18 without having to worry about achieving a successful locking orientation and having to reposition a bone screw to ensure a locked configuration. In other words, if due to the patient anatomy, the bone screw 18 placement is highly askew, the rotating lock of the present invention can be rotated in a clockwise or counterclockwise direction and between 0 and 180 degrees to cover a bone screw 18 to achieve back out protection; whereas, in other designs of cages that require a plate to cover the screw heads, the cover plate may not be able to be positioned due to a projecting or askew bone screw and as a result requiring a tradeoff between bone screw positioning/re-positioning and back-out protection. The present invention advantageously offers wide flexibility for bone screw placement while at the same time offering a wide coverage for a locked configuration of one or more bone screws. In another variation, the main body of the screw lock is not symmetrical in a cross-section taken perpendicular to the longitudinal axis of the screw lock and may be, for example, lobed in one direction.

As mentioned above, the screw lock 100 is rotatable with respect to the cage 12. In one variation, a freely rotating screw lock 100 is provided in which the post 66 is not faceted with flat sides. In the variation shown in the figures, the screw lock 100 is free to rotate; however, metered, incremental rotation of the lock assembly 16 with respect to the cage 12 is provided due to the timing lock 102 and its interaction with flat faceted sides 78 of the screw lock 100. The faceted post 66 advantageously prevents inadvertent movement or rotational migration of the main body 64 of the screw lock 100 into the insertion pathway of the bone screw 18 and, thereby, prevents interference with bone screw placement. To rotate the screw lock 100, an instrument having a distal end that is complementary to the size and shape of the socket 72 formed in the top surface 70 of the main body 64 is used. As the screw lock 100 is rotated from the unlocked position in either a clockwise or counterclockwise direction, the diagonal distance of the cross-section of the neck 76 taken perpendicular to the longitudinal axis of screw lock 100 will come into contact and engage the lock-engaging the prong faces 94 of the timing lock 102. Since the diagonal distance or length, as measured from the center of one beveled corner 80 to the center of another beveled corner 80 that is located diagonally across is longer than the side 78 to side 78 distance width of the post, rotation of the screw lock 100 will splay the prongs 92 slightly apart in a cam-like action before snapping into a completed approximately 90 degree rotation of the screw lock 100 around its longitudinal axis in which two opposite sides 78 will come into juxtaposition or engagement with the prong faces 94. The cross-sectional shape of the post 66 in the location of the flat sides 78 and their engagement with the prong faces 94 provide an incremental or timed rotation of 90 degrees. The post can have any irregular shape such that its rotational motion gives the prongs that are in contact with the post a specific rocking or reciprocating cam-like motion. The cross-section of the post 66 may have a different number of facets than the four sides shown in the figures. For example, the post 66 can have three sides to form a triangular-shaped cross-section or an octagonal shaped cross-section as seen fit to increase the number of increments in the rotation around the perimeter and reduce the arc of rotation as needed. The incremental rotation advantageously provides tactile feedback to the surgeon of successfully establishing a locked configuration as well as to the number of rotations of the lock.

In addition to the advantages of the interbody spacer 10 of the present invention noted above, the interbody spacer 10 according to the present invention provides a preassembled cage and lock assembly. This assembly advantageously allows the surgeon to simply position the implant between vertebrae, drive the bone screws into the bone and rotate the lock into a locked configuration. The surgeon is not required to pick-and-place a cover plate onto the anterior side of the cage to cover the bone screws. The surgeon is also not required to pick-and-place a plate screw and drive the plate screw to secure the cover plate to the cage either in-situ or in assembly.

In use, the present interbody spacer 10 is configured for use as an anterior cervical cage in spinal surgical procedures. It is understood that novel features of the present invention can find application in different types of cages including but not limited to interbody spacers for ALIF, PLIF, TLIF, XLIF surgical procedures as well as other types of orthopedic implants. Implanting the interbody spacer 10 involves removal, in whole or in part, of the disc material from the intervertebral space at the target vertebral level where the interbody spacer 10 will be implanted. The patient is oriented to provide some distraction of the disc space and to provide access to the anterior of the spine. Additional distraction of the disc space and surrounding tissues may be needed to decompress the nerve roots, realign the anatomical axis of the spine, and restore disc space height at the particular target level. After disc material is removed, a clean space is achieved in which to place the device. The vertebral endplates may be further prepared using burrs, curettes and the like to abrade and clean the endplates to encourage bone regeneration. A surgeon will then select an appropriately sized cage 12 that has the best size in footprint and height and lordotic angle for the target space. The surgeon may use an insertion instrument to grasp the cage 12 and place it at the mouth of the intervertebral space and move and orientate the cage 12 into its proper orientation within the intervertebral space. The insertion instrument typically has two distal prongs configured to securely attach to the cage 12 at the instrument notches 42. The surgeon may determine the position of the cage 12 with the help of one or more x-ray fluoroshots. Since the position of the radiographic markers are known relative to the cage 12, a surgeon can determine the position of the cage 12 in the target space by viewing the positions of the radiographic markers embedded in the cage 12 that appear in the x-ray and reposition the cage 12 as needed until final placement is achieved. The cage 12 may include bone graft or other material located inside the central opening 44 of the cage 12 to promote ingrowth and blood supply in order to grow active and live bone from the adjacent spinal vertebrae to inter-knit with the spacer 10 and, thereby, eventually immobilize and fuse the adjunct spinal vertebrae. The cage 12 is placed such that the anterior surface 30 of the cage 12 faces the anterior side of the patient and the top surface 24 contacts the lower endplate of the upper vertebral body and the bottom surface 26 of the cage 12 contacts the upper endplate of the lower vertebral body on either side of the target intervertebral space. The geometry of the ridges 48 on the top surface 24 and the bottom surface 26 provide resistance to migration of the cage 12 while inside the target space. Other coatings and surface textures may also be provided on the cage 12. Next, bone screws 18 are deployed via a surgical instrument such as a bone screw driver. The bone screws 18 are inserted into the bone screw apertures 54 and tapped into the bone of the adjoining vertebral bodies. The one or more bone screws 18 are passed through the cage 12 via the bone screw apertures 54 in a trajectory transverse to the longitudinal axis and into the upper and lower vertebral bones. As the bone screws 18 are tightened, the vertebral bodies penetrated with the bone screws 18 will compress onto both sides of the load-bearing cage 12 and provide pressure to help facilitate fusion. Additional bone graft material may be placed in the intervertebral disc space. Next, the screw locks 100 are rotated clockwise or counterclockwise as needed with an instrument inserted to the socket 72 of the screw lock 100 to bring the screw lock 100 from an unlocked configuration to a locked configuration to provide an anti-backout mechanism to prevent the bone screws 18 from loosening and/or exiting the cage 12. With the lock assembly 16 in a locked configuration, the screw lock 100 is disposed over a head 118 of at least one of the adjacent bone screws 18 implanted together with the cage 12. The lock provides anti-back-out protection for the bone screws 12. In one variation, because the bone screws 18 are partially covered, the bone screws are permitted to angulate at a greater angle. The bone screws 18 are shown at a given angle although any suitable angle(s) for a given application may be utilized and as may any suitable number of screws. Additional instrumentation such as rods or screws may also be used to further stabilize the spine across the target level. Any of the components in the present invention are manufactured from metal such as titanium, ceramic, plastic such as PEEK and carbon fiber reinforced polymer, biomaterial including but not limited to any of a number of biocompatible implantable polymers including PEKK, PEKEK, polyetheretherketone (PEEK) being preferred, titanium ceramic, bone or other material etc. The present invention can be employed and is suitable for use where ever the backing out of screws is to be prevented and anywhere along the spine including but not limited to cervical, thoracic, lumbar or sacral or between other bony structures outside of the spinal region. Embodiments of the present invention are standalone interbody devices which may be designed in the general style of an ALIF device, TLIF device, PLIF device or other device. In addition, the size and/or shape of the basic embodiments disclosed herein may be adapted by one skilled in the art for use in various levels of the spine, namely the cervical spine, thoracic spine and the lumbar spine. Thus, while various embodiments herein may be described by way of example with respect to the cervical spine such disclosures apply with equal weight to the other levels of the spine.

It is understood that various modifications may be made to the embodiments of the interbody spacer disclosed herein. Therefore, the above description should not be construed as limiting, but merely as exemplifications of preferred embodiments. Those skilled in the art will envision other modifications within the scope and spirit of the present disclosure.

We claim:
1. An interbody spacer for a spine, comprising:
a cage having a top surface and a bottom surface interconnected by a sidewall; the cage includes a central opening extending between the top surface and the bottom surface and defining an inner surface; the cage includes at least one bone screw aperture in the sidewall; the cage includes a lock aperture; the lock aperture being sized and configured to receive a screw lock;
at least one bone screw disposed inside the at least one bone screw aperture; each bone screw having a head at a proximal end and a threaded shank extending toward a distal end for anchoring into bone; the bone screw being configured to secure the interbody spacer between two bony components of the spine; and
a screw lock connected to the cage and located inside the lock aperture; the screw lock including a main body connected to a post; the post being located inside the lock aperture; the screw lock having an unlocked position in which the screw lock does not cover the head of the bone screw inside the bone screw aperture permitting passage of the bone screw in or out of the bone screw aperture and a locked position in which the main body of the screw lock is above the head of the bone screw to prevent the bone screw from backing out of the bone screw aperture; wherein rotation of the screw lock moves the screw lock between the unlocked position and the locked position; and
a collar located around the screw lock and configured to provide incremental rotation of the screw lock; wherein the screw lock is rotatable with respect to the collar.

2. The interbody spacer of claim 1 further including a retaining ring connected to the screw lock such that the screw lock is retained and rotatable with respect to the cage; the post extending into the central opening and the retaining ring abutting the inner surface of the cage.

3. The interbody spacer of claim 1 wherein the collar includes a base with at least one prong extending from the base; the at least one prong having a prong face and the post having at least one flat surface; the collar being coupled to the screw lock such that the at least one prong face is facing the at least one flat surface along the rotation of the screw lock relative to the collar; wherein the collar resists rotation of the screw lock when the at least one prong face is not facing the at least one flat surface.

4. The interbody spacer of claim 3 wherein the lock aperture includes at least one side aperture sized and configured to receive the at least one prong of the collar and fix rotational movement of the collar relative to the cage.

5. The interbody spacer of claim 3 further including a retaining ring connected to the screw lock such that the screw lock is retained and rotatable with respect to the cage; the post extending into the central opening and the retaining ring abutting the inner surface of the cage.

6. The interbody spacer of claim 1 wherein the collar includes two oppositely disposed prongs each having a prong face; the post having four oppositely disposed flat surfaces the prong faces being oppositely disposed and configured to face the two oppositely disposed flat surfaces along the rotation of the screw lock relative to the collar.

7. The interbody spacer of claim 6 wherein the lock aperture includes two side apertures sized and configured to receive the two prongs of the collar and fix rotational movement of the collar relative to the cage.

8. The interbody spacer of claim 1 wherein the post has a cross-section taken perpendicular to the longitudinal axis of the screw lock; the cross-section having a length and a width; the length being longer than the width; wherein rotation of the screw lock relative to the collar imparts a biasing force onto the screw lock.

* * * * *